(12) United States Patent
Naraghi et al.

(10) Patent No.: US 10,022,113 B2
(45) Date of Patent: Jul. 17, 2018

(54) METHODS, SYSTEMS, AND DEVICES FOR THE TREATMENT OF STENOSIS

(71) Applicants: Fred F. Naraghi, San Francisco, CA (US); Brandon Naraghi, San Francisco, CA (US)

(72) Inventors: Fred F. Naraghi, San Francisco, CA (US); Brandon Naraghi, San Francisco, CA (US)

( * ) Notice: Subject to any disclaimer, the term of this patent is extended or adjusted under 35 U.S.C. 154(b) by 283 days.

(21) Appl. No.: 14/923,609

(22) Filed: Oct. 27, 2015

(65) Prior Publication Data
US 2016/0045192 A1    Feb. 18, 2016

Related U.S. Application Data

(63) Continuation-in-part of application No. 14/492,537, filed on Sep. 22, 2014.

(60) Provisional application No. 61/880,372, filed on Sep. 20, 2013.

(51) Int. Cl.
| | |
|---|---|
| *A61B 17/02* | (2006.01) |
| *A61M 29/02* | (2006.01) |
| *A61B 17/88* | (2006.01) |
| *A61B 17/00* | (2006.01) |
| *A61B 90/00* | (2016.01) |
| *A61B 17/32* | (2006.01) |

(52) U.S. Cl.
CPC ...... *A61B 17/0218* (2013.01); *A61B 17/8855* (2013.01); *A61B 2017/00557* (2013.01); *A61B 2017/320048* (2013.01); *A61B 2090/063* (2016.02); *A61B 2090/064* (2016.02); *A61B 2090/3925* (2016.02); *A61B 2090/3966* (2016.02); *A61M 29/02* (2013.01)

(58) Field of Classification Search
None
See application file for complete search history.

(56) References Cited

U.S. PATENT DOCUMENTS

| | | |
|---|---|---|
| 5,902,254 A | 5/1999 | Magram |
| 6,719,795 B1 | 4/2004 | Cornwall et al. |
| 8,114,161 B2 | 2/2012 | Evans et al. |
| 8,147,516 B2 | 4/2012 | Malandain et al. |
| 8,147,526 B2 | 4/2012 | Auyoung |
| 8,152,837 B2 | 4/2012 | Altarac et al. |
| 8,167,890 B2 | 5/2012 | Malandain et al. |
| 8,167,944 B2 | 5/2012 | Kim |

(Continued)

OTHER PUBLICATIONS

International Preliminary Report on Patentability for PCT/US11/33450 dated Aug. 7, 2012.

(Continued)

*Primary Examiner* — Thomas McEvoy
(74) *Attorney, Agent, or Firm* — Ryan Kromholz & Manion, S.C.

(57) ABSTRACT

Catheter system, devices and methods for diagnosing and treating lateral stenosis causing back pain and or leg pain. The devices comprise a tubular part for insertion into a working cannula to self-position itself safely within the foramen, and minimize the risk of displacement medially or laterally, to prevent nerve or dura injury. An expandable membrane is configured to maintain the catheter device within the foramen. Expansion of this membrane would decompress the nerve within the foramen by opening the foraminal canal as the membrane expands. Inserts may be used in connection with the expandable member.

12 Claims, 25 Drawing Sheets

(56) References Cited

U.S. PATENT DOCUMENTS

| | | |
|---|---|---|
| 8,187,327 B2 | 5/2012 | Edidin et al. |
| 8,192,435 B2 | 6/2012 | Bleich et al. |
| 2002/0022830 A1 | 2/2002 | Sharkey et al. |
| 2006/0084987 A1 | 4/2006 | Kim |
| 2006/0235387 A1 | 10/2006 | Peterman |
| 2008/0208341 A1 | 8/2008 | McCormack et al. |
| 2009/0062871 A1 | 3/2009 | Chin et al. |
| 2009/0204150 A1 | 8/2009 | Hochschuler et al. |
| 2010/0100133 A1 | 4/2010 | Carl et al. |
| 2010/0100183 A1 | 4/2010 | Prewett et al. |
| 2011/0288553 A1 | 11/2011 | Jansen et al. |
| 2015/0088185 A1 | 3/2015 | Naraghi et al. |
| 2016/0045192 A1 | 2/2016 | Naraghi et al. |

OTHER PUBLICATIONS

International Search Report and the Written Opinion of the International Searching Authority dated Jan. 17, 2017, from PCT/US2016/058646.

METHODS, SYSTEMS, AND DEVICES FOR THE TREATMENT OF STENOSIS

RELATED APPLICATIONS

This application is a continuation-in-part of application Ser. No. 14/492,537, filed on Sep. 22, 2014, which claims the benefit of U.S. provisional application Ser. No. 61/880,372 filed on Sep. 20, 2013.

FIELD OF INVENTION

The present invention relates to devices and apparatus for the treatment of stenosis, and particularly the use of catheter devices in combination with an expandable device for the treatment of stenosis.

BACKGROUND OF THE INVENTION

Disc herniation and degenerative disorders of the lumbar spine are prevalent, deteriorate the quality of life, and are a major health care concern of the general population.

Lumbar spinal stenosis is defined as the narrowing of the spinal canal in the lumbar region. This is as a consequence of several pathologic conditions, the most common of which is chronic degenerative spondylosis. Other common causes of stenosis include disc herniation, facet hypertrophy, or congenital causes. Absolute stenosis has been defined as a decrease in the midsagittal lumbar canal diameter of less than 10 mm on MRI.

Although there are different ways of describing stenosis, generally the stenosis of the spinal canal can occur centrally or laterally. Patients often present with a combination of symptoms from both central and lateral stenosis.

Lateral stenosis can be further classified into three distinct zones: the lateral recess, foraminal zone, and extraforaminal zone.

Lateral recess stenosis is caused by overgrowth of the superior articular facet, and ligamentum or capsular redundancy or hypertrophy. Foraminal stenosis may be due to a foraminal disk protrusion, posterior osteophyte formation, ligamentum or capsular hypertrophy, or loss of vertical height from degenerative collapse of the disk. The extraforaminal zone, which is defined as the area lateral to the intervertebral foramen, is most often affected by far-lateral disk and osteophyte pathology.

Spinal nerves (also referred to as "nerve roots") originate from the spinal cord, remain within the central portion of the spinal canal, and then exit through the foramen or neuroforamen. The neuroforamen primarily contains the nerve root exiting from each corresponding intervertebral level. It also contains the dorsal root ganglion (DRG), a structure that contains the cell bodies of the afferent sensory neurons. DRG has a variety of sensory receptors that are activated by mechanical, thermal, chemical, and noxious stimuli. If DRG is impinged within the foramen, in lateral stenosis cases, it can be quite painful, and it can become a major source of pain generation.

Spinal stenosis is treated conservatively initially with therapy modalities and medications. Epidural injections with local anesthetics and steroids may be used next. However, these injections may relieve pain for a limited period of time only. More importantly, injections typically do not influence or improve the functional outcome of patient condition. The majority of patients report little substantial improvement in symptoms with repeated treatment.

Decompression surgery is considered only after conservative treatments have failed. Currently, there are 2 surgical approaches to decompress the lateral portion of the canal: medial (or "inside-out"), and lateral (or "outside-in", or "transforaminal"). Each has its advantages and disadvantages. The advantage of the medial approach includes surgeon familiarity through a laminotomy. The disadvantage of medial approach is significant bone resection required to get to the foramen, which is located more laterally, and possible dural tear. This excess bone resection may lead to an iatrogenic instability of the spinal segment if it is extensive. Also, trying to reach under the facet to decompress the foraminal zone can result in possible injury to the nerve root injury due to the deep and lateral position of the nerve root within the foramen. The advantage of transforaminal approach includes less or no bone resection, less risk of dural tear, faster recovery due to less muscle dissection, less risk of possible epidural scar formation. The disadvantages of transforaminal approach include technically demanding approach, and difficulty in visualizing the content of foramen from the lateral side.

Balloon dilation is currently used in various parts of the body including esophagus, urethra, coronary arteries, and peripheral arteries. Additionally, balloons have been used to create a void within vertebral body to restore the height of fractured vertebrae and allow for filling of the void with cement or bone graft to stabilize a vertebral fracture, commonly referred to as Kyphoplasty.

Balloons have also been used to aid in separating tissues or vital structures away from a targeted area to be addressed surgically in various parts of the body, including abdominal surgery.

However, the prior art devices or techniques have not addressed the performing a less invasive open or percutaneous decompression of the lateral stenosis through the use of balloons.

The use of balloons in the neuroforamen has been discussed in the prior art, but has not addressed the main problem of having adequate control of the balloon device and the method to specifically localize and target a specific point within the neuroforamen.

SUMMARY OF THE INVENTION

The present invention is directed towards the use of systems and devices that employ catheter devices in combination with expandable structures, e.g. balloons, to treat stenosis. The balloons are utilized to perform foraminal decompression, which allows for non-surgical or less invasive surgical treatment of lateral spinal stenosis by modifying the underlying pathophysiology.

In one embodiment of the present invention, the expandable structure of the present invention is positioned within the foramen of the spine, with the structure used for decompression of spinal stenosis. The present invention may be used for decompression of lateral spine stenosis. For example, the present invention may be used for decompression in the lateral recess zone, the foraminal zone, or the far lateral (or extraforaminal zone of the spinal canal.

The methods of the present invention include using the systems and methods used for treating stenosis. The methods can be used for treating spinal stenosis.

The methods of the present invention include advancing the catheter and inflatable member into the spinal area near where the stenosis occurs. The inflatable member will be advanced, partially inflated, with the steps repeated until proper positioning of the inflatable member to address the stenosis.

The inflatable members used in the present invention can be of varying sizes, shapes, and materials.

The inflatable members of the present invention provide selective control of the location of the inflatable member into the spinal area.

The present invention also includes inserts of various shapes, sizes and texture to be used to provide selective control for treating stenosis.

The present invention also includes combinations of inflatable members and inserts for treating stenosis.

DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention. While the present invention pertains to systems, devices, and surgical techniques applicable at virtually all spinal levels, the invention is well suited for achieving dynamic stabilization of transverse processes of adjacent lumbar vertebrae. It should be appreciated, however, the systems, device, and methods so described are not limited in their application to the spine, and could be employed for use in treating different types of stenosis throughout the body.

Figure 1:
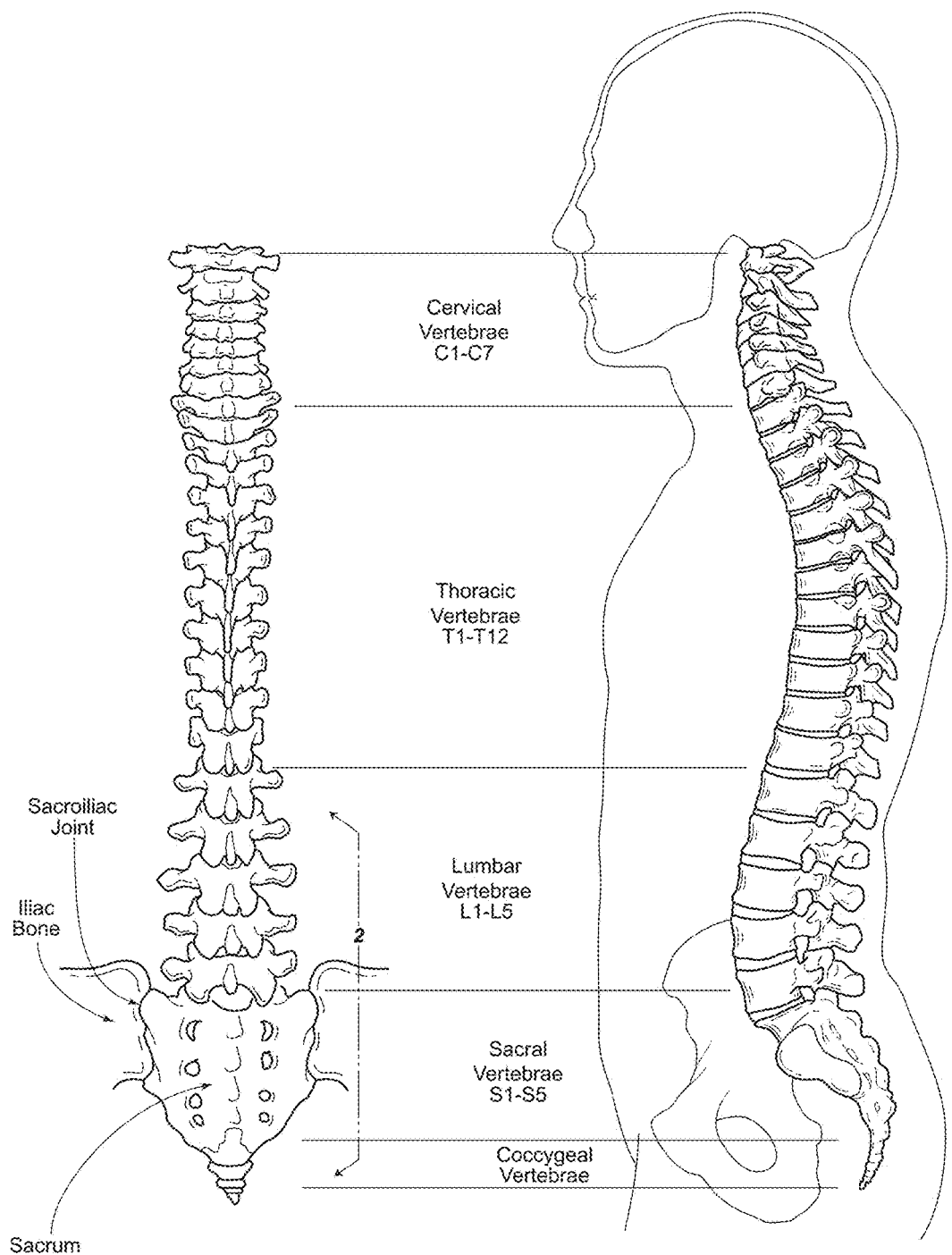
FIG. 1 is an anatomic view of a human spine, showing the different regions of vertebrae.

The spine (see FIG. 1) is a complex interconnecting network of nerves, joints, muscles, tendons and ligaments. The spine is made up of small bones, called vertebrae, which are named according to the region of the body they occupy. The vertebrae in the head and neck region are called the cervical vertebrae (designated C1 to C7). The vertebrae in the neck and upper back region are called the thoracic vertebrae (designated T1 to T12). The vertebrae in the lower back region are called the lumbar vertebrae (numbered L1 to L5). The vertebrae in the pelvic region are called the sacral vertebrae (numbered S1 to S5).

Figure 2:
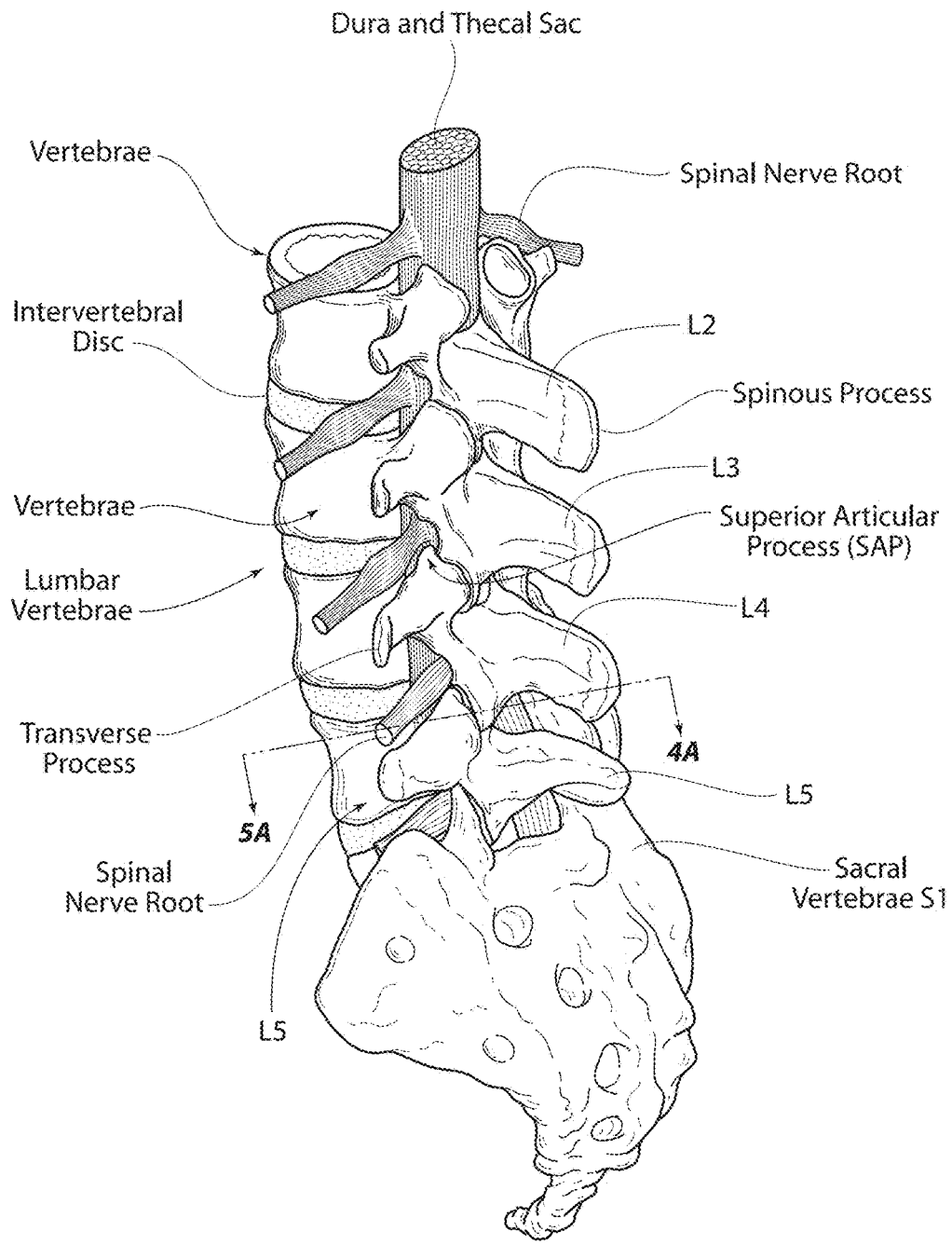
FIG. 2 is an anatomic ipsilateral view of the lower back region of the spine, showing the lumbar vertebrae L2 to L5, the sacral vertebrae S1 to S5, and the coccygeal vertebrae.
Figure 3:
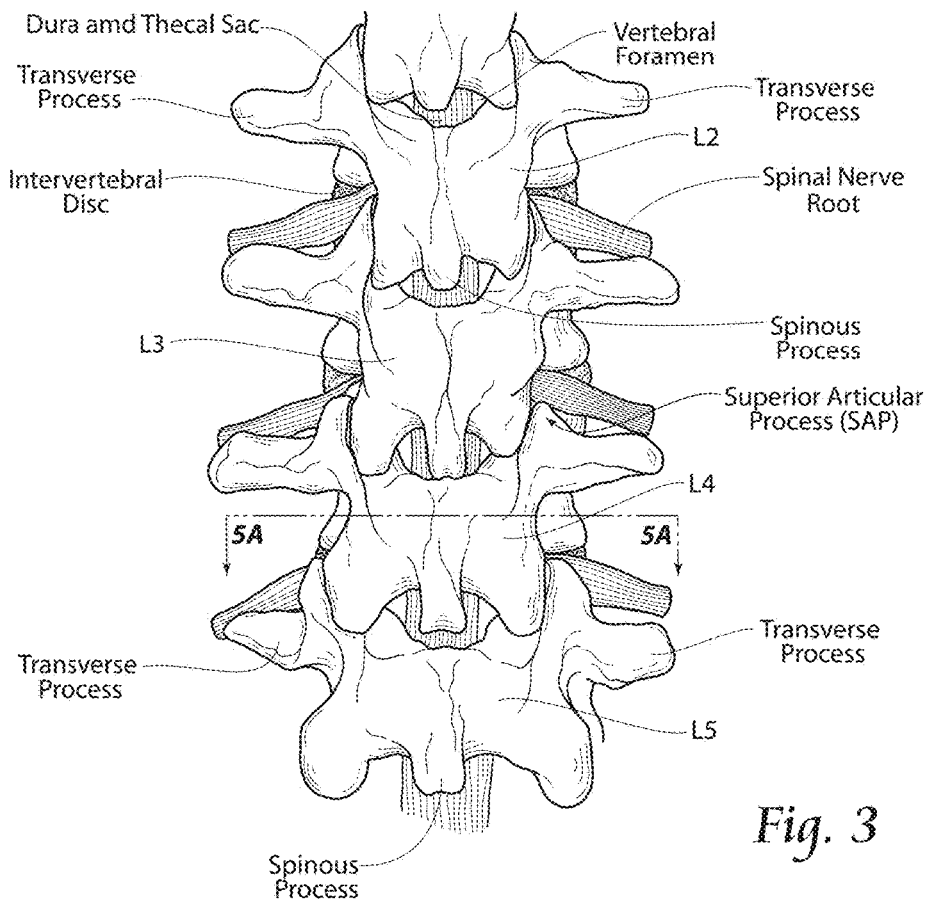
FIG. 3 is an anatomic posterior view of the lower back region of the spine, showing the lumbar vertebrae L2 to L5.
Figure 4:
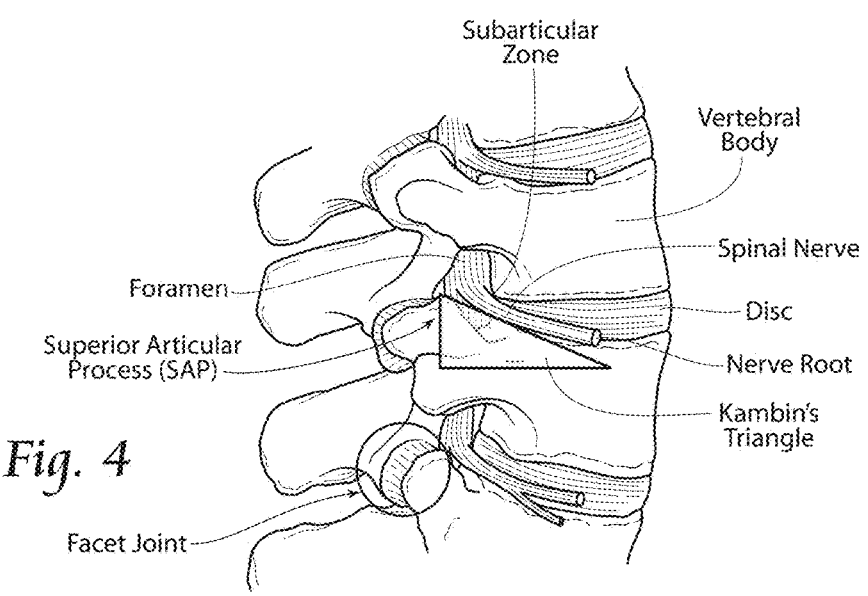
FIG. 4 is an anatomic distal view of the view of the spine shown in FIG. 3.

The vertebrae protect and support the spinal cord. They also bear the majority of the weight put upon the spine. As can be seen in FIG. 4A, vertebrae, like all bones, have an outer shell called cortical bone (the vertebral body) that is hard and strong. The inside is made of a soft, spongy type of bone, called cancellous bone. The bony plates or processes of the vertebrae that extend rearward and laterally from the vertebral body provide a bony protection for the spinal cord and emerging nerves. The vertebrae also protect the thecal sac as shown in FIGS. 2 and 3. The thecal sac contains the nerve roots for the spinal cord. The spinal cord ends around L1-L2 vertebrae, with the thecal sac continuing downwardly from there.

The configuration of the vertebrae differ somewhat, but each (like vertebrae in general) includes a vertebral body (see FIG. 5A), which is the anterior, massive part of bone that gives strength to the vertebral column and supports body weight. The vertebral canal is posterior to the vertebral body and is formed by the right and left pedicles and lamina. The pedicles are short, stout processes that join the vertebral arch to the vertebral body. The pedicles project posteriorly to meet two broad flat plates of bone, called the lamina. The arrangement can also be viewed in FIG. 4.

Other processes arise from the vertebral arch. For example, two superior articular processes ("SAP") project upward from vertebral arch and provide an area for adjacent vertebrae to fit together with one another. Three other processes—the spinous process and two transverse processes—project from the vertebral arch and afford attachments for back muscles, forming levers that help the muscles move the vertebrae.

FIG. 2 shows the S1 sacral vertebra and the adjacent fourth and fifth lumbar vertebrae L4 and L5, respectively, in a lateral view (while in anatomic association). The sacral and lumbar vertebrae are in the lower back, also called the "small of the back." FIG. 3 shows the fourth and fifth lumbar vertebrae L4 and L5 from a different, more posterior, perspective.

Figure 5A:
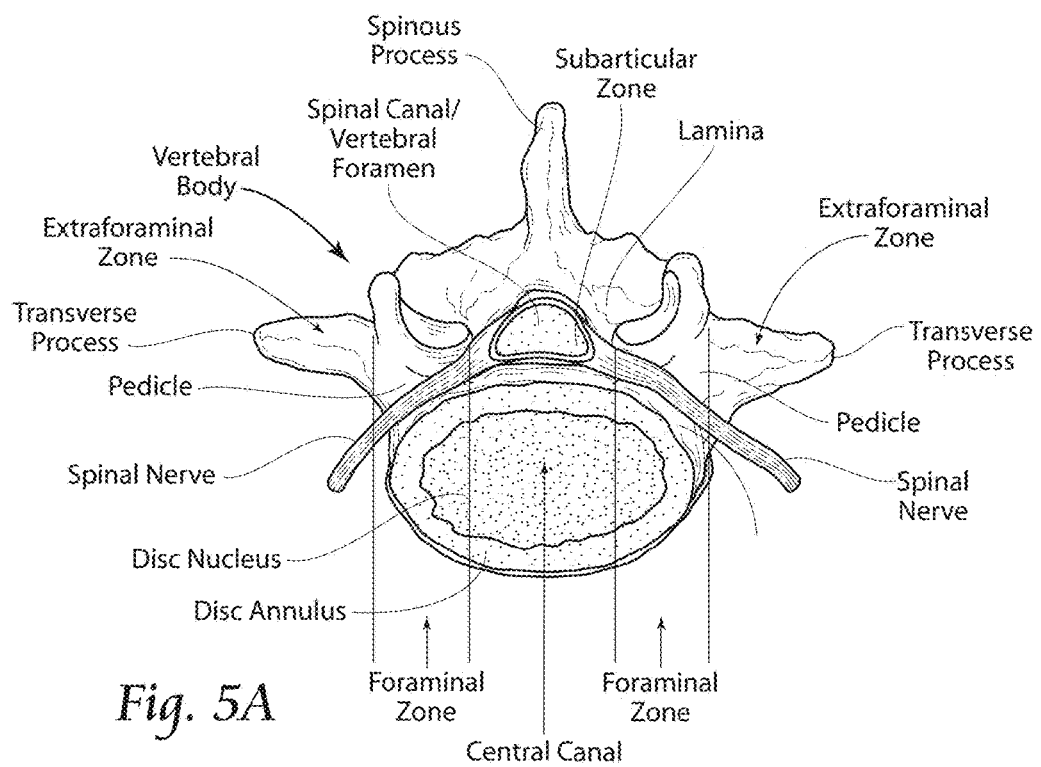
FIG. 5A is an anatomic superior view of a vertebral body, taken along line 5A-5A of FIG. 3, depicting the central canal, foraminal zone, and the extraforaminal zone of the vertebral body.

As previously described, between each vertebra is a soft, gel-like "cushion," called an intervertebral disc (see FIG. 2). These flat, round cushions act like shock absorbers by helping absorb pressure and keep the bones from rubbing against each other. The intervertebral disc also binds adjacent vertebrae together. The intervertebral discs can bend and rotate a bit but do not slide. Along with the invertebral discs, the vertebrae also provide protection for the spinal cord and thecal sac by forming the vertebral foramen (FIG. 5A). The foramen may be depicted with three zones, the foraminal zone, the central canal, and the extraforaminal zone. Stenosis may occur in any of these zones of the foramen, and it is intended that the methods and systems of the present invention would address stenosis in any of these areas.

Figure 5B:
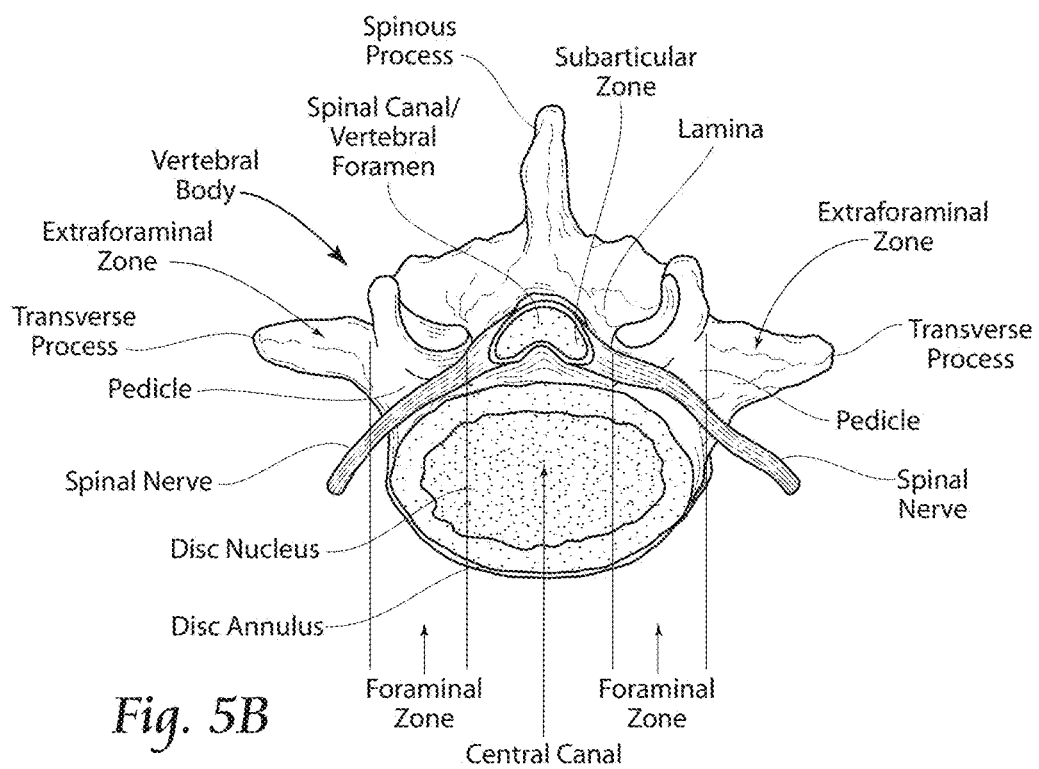
FIG. 5B is an anatomic superior view of a vertebral body, taken along line 5A-5A of FIG. 3, but showing spinal stenosis affecting the region.

FIG. 5A shows a vertebra with a normal vertebral foramen. The vertebral foramen provides an open spinal canal for the spinal cord and the thecal sac to reside. FIG. 5B shows a vertebra with abnormal narrowing of the vertebral foramen, e.g. showing spinal stenosis. As previously explained, when spinal stenosis occurs, the spinous process overgrows into the vertebral foramen, thereby impinging on the spinal cord and/or the thecal sac and the related spinal nerves. The impingement into the vertebral foramen causes nerve root compression and spinal stenosis, with resulting pain, and discomfort.

As previously discussed, each vertebra also has two other sets of joints (see FIGS. 2 and 3). For a given vertebra (e.g., L4), one pair of facet joints faces upward (called the superior articular process, SAP) and the other pair of facet joints faces downward (called the inferior articular process, IAP). The inferior and superior processes mate, allowing motion (articulation), and link vertebrae together. Facet joints are positioned at each level to provide the needed limits to motion, especially to rotation and to prevent forward slipping (spondylolisthesis) of that vertebra over the one below.

Figure 6A:
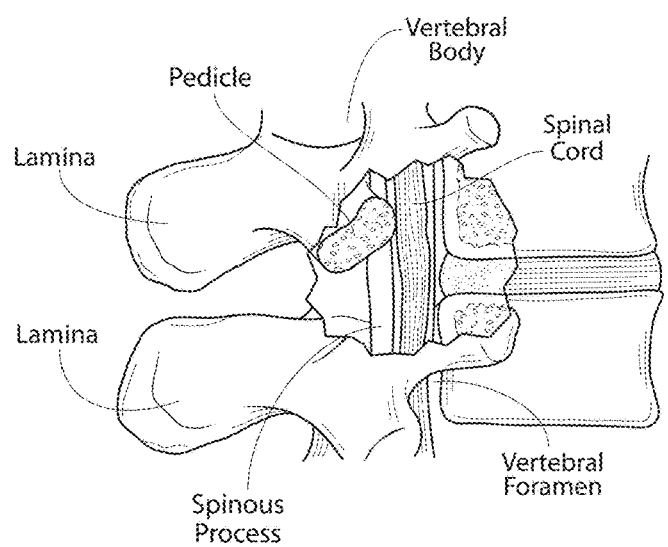
FIG. 6A is a partially cut-away view of the spinal region as shown in FIG. 3.
Figure 6B:
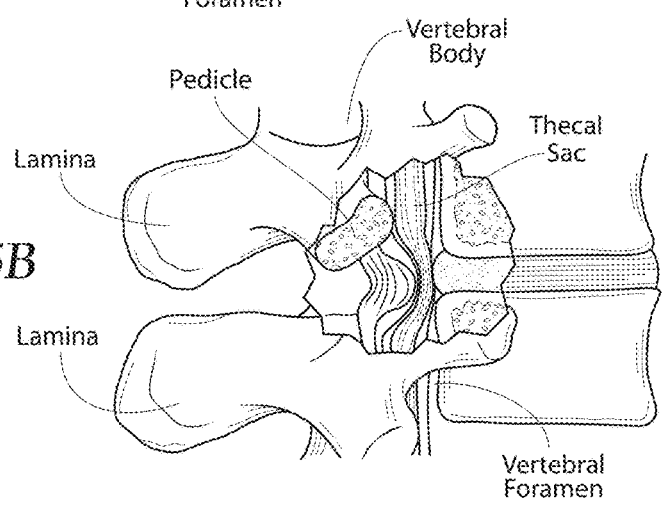
FIG. 6B is a partially cut-away view of the spinal region as shown in FIG. 3, but showing spinal stenosis in the region.

FIGS. 6A and 6B provide another perspective to demonstrate the anatomy shown and described in FIGS. 5A and 5B. The partially cut-away view in FIG. 6A shows the thecal sac sitting within the vertebral foramen, being protected by the vertebral body, as described above. However, as shown in FIG. 6B, an impingement of the thecal sac is shown. The disc is pushing into the thecal sac, while the vertebral facet pushes forward into the thecal sac. Such an impingement is often a condition of facet hypertrophy, or an enlargement or degenerative change in the facet joint. These degenerative changes in the spinous process and the spine in general can adversely affect the ability of each spinal segment to bear weight, accommodate movement, and provide support. When one segment deteriorates to the point of instability, it can lead to localized pain and difficulties.

Facet joint fixation procedures have been used for the treatment of pain and the effects of degenerative changes in the lower back. In one conventional procedure for achieving facet joint fixation, the surgeon works on the spine from the back (posterior). The surgeon passes screws from the spinous process through the lamina and across the mid-point of one or more facet joints.

II. Representative System of a Delivery Device Used in Treating Stenosis

The present invention is directed towards a system for treating and addressing conditions caused by stenosis of the joints and is particularly useful for treatment of spinal stenosis. The system will provide relief of the vertebral column and the discs from impinging on the spinal cord and/or thecal sac located in the vertebral foramen.

Figure 8:
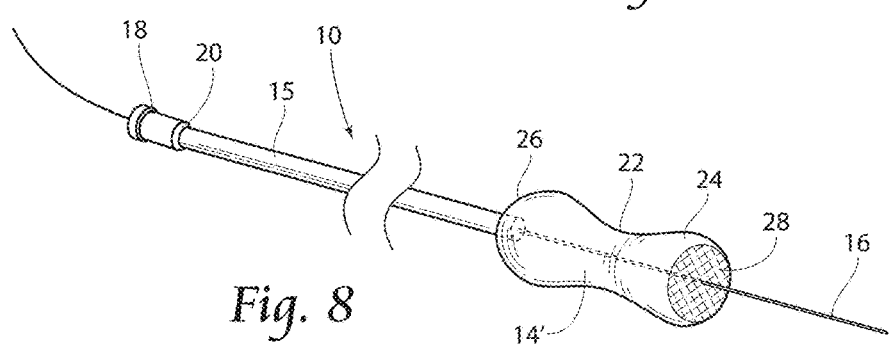
FIG. 8 is partial cut-away perspective view of a delivery device of the present invention, with the inflatable member being inflated and a guide wire within the inflatable member.

As shown in FIG. 8, the system 10 generally comprises a catheter 12 that houses an expandable member 14, 14', e.g. a balloon. As will be discussed in further detail, the catheter will generally be introduced into the vertebral foramen by way of a working cannula 15. The system may also include a guide wire 16 to assist in directing the catheter into the vertebral foramen. Preferably the guide wire 16 is attached to the working cannula 14 at the proximal end 18 by a screw fitting 20 or other common arrangement that will allow the guide wire to be attached or removed as necessary.

Figure 7A:
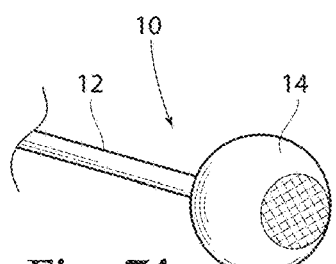
FIG. 7A is a partial view of a delivery device 10 of the present invention being used in the present invention, with a generally spherical inflatable member being used within the delivery device.
Figure 7B:
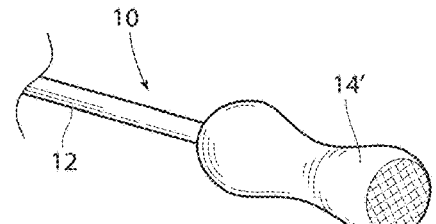
FIG. 7B is a partial view of a delivery device as shown in FIG. 7A, with the exception that the inflatable member has a generally barbell shape.

FIGS. 7A and 7B demonstrate different shaped expandable members 14, 14' that may be used in the system. In FIG. 7A, a spherical expandable member 14 is shown, while a dumbbell-shaped expandable member 14' is shown in FIG. 7B. The dumbbell-shaped expandable member 14' may be designed so that the middle section 22 is less expandable than the distal 24 and proximal portions 26 (see FIG. 8). In certain situations, as discussed below, such an arrangement will provide for the expandable member 14' to act as anchor between the medial and lateral sides of a vertebral facet joint. The expandable member 14' may be made of differing materials that allow the distal 24 and proximal portions 26 to expand quicker than the central portion 22 of the expandable member 14'.

Figure 9:
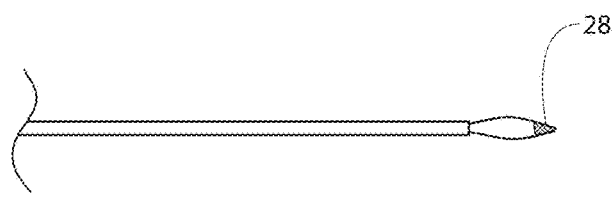
FIG. 9 is a partially cut-away view of the delivery system of the present invention, demonstrating a radiopaque marker on the inflatable member.
Figure 10:
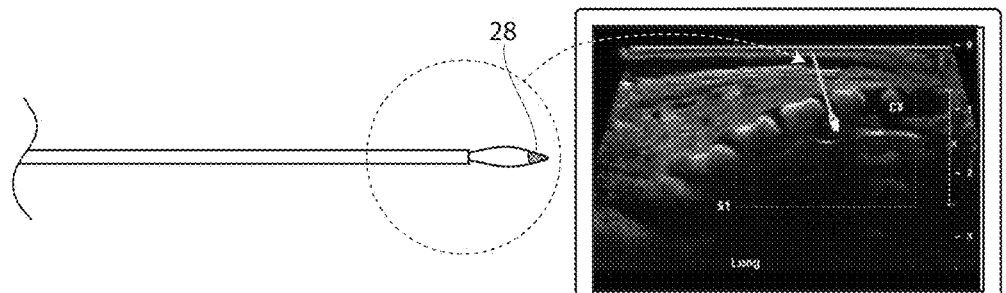
FIG. 10 is a partially cut-away view of the delivery system of the present invention, demonstrating an echogenic marker on the inflatable member in combination with an ultrasound imaging machine.

To assist in proper positioning of the expandable member 14, 14', a marker 28 may be located on the end or tip of the expandable member. For example, a radiopaque marker (demonstrated in FIG. 9) may be used to visualize the expandable member 14, 14' position during fluoroscopy. Alternatively, an echogenic marker (demonstrated in FIG. 10) could be used in combination with an ultrasound device for ultrasonic guidance of the expandable member 14, 14'.

To assist in the treatment of stenosis, the catheter 12 is also designed so that the pressure within the expandable member 14, 14' can be measured, so that proper positioning of the expandable member 14, 14' when deployed will occur. The volume may also be measure, for example with the use of a dyed fluid being injected into the expandable member.

The system is also designed so that various solutions, treatments, and substances can be injected into the treated area. For example, anesthetics, steroids, growth factors, stem cell material, or other medicinal materials, may be injected through the system into the treated foraminal space.

As will be discussed below, the system 10 is designed so that the expandable members can be advance into the vertebral foramen to address the stenosis and, eventually, removed from the foramen once the stenosis has been addressed.

III. Representative Methods for the Treatment of Stenosis

The present invention includes methods for the treatment of stenosis. As generally discussed above, stenosis is caused by an impingement into a foramen, thereby constricting the thecal sac, nerves, or spinal cord that may be located within the foramen. The methods generally are directed towards the use of expandable members 14, 14' such as balloons that are inserted into the foramen. The expandable members are inflated in a step-like process to treat the impingement.

As demonstrated below, the methods of the present invention can be used for the treatment of spinal stenosis. Spinal stenosis may be caused by the overgrowth of the superior articular facet, ligamentum, capsular redundancy, hypertrophy, or a combination of these. As described below, there are two main ways of addressing the spinal stenosis according to the present invention: 1) a mid-line approach that would generally be performed during a laminotomy, or 2) a percutaneous approach.

Furthermore, the methods described below address issues and problems of the prior art, namely having adequate control of the inflatable members 14, 14' used in the methods. The described methods are capable of being directed to specifically localize and target a specific point within the neuroforamen. As will be discussed, the present invention allows for control of the inflation of the discussed inflatable members 14, 14', including control of variables such a pressure and volume for the inflatable members, which allows for precise treatment of the stenosis.

Figure 11:
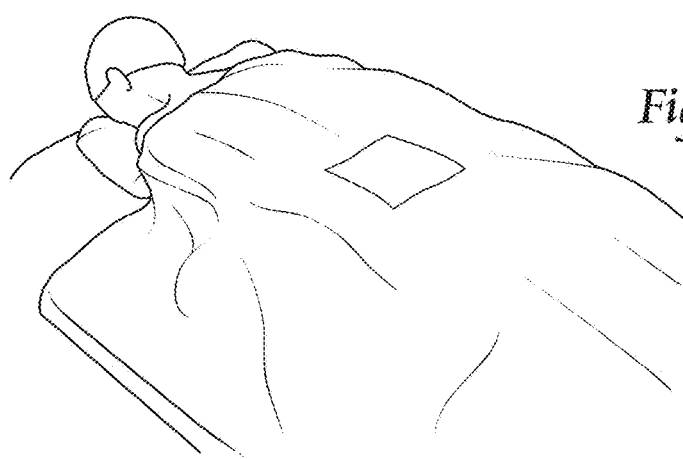
FIG. 11 depicts a patient lying on an operating table, with the patient's back exposed, which demonstrates an initial step in performing a procedure according to the present invention.
Figure 12:
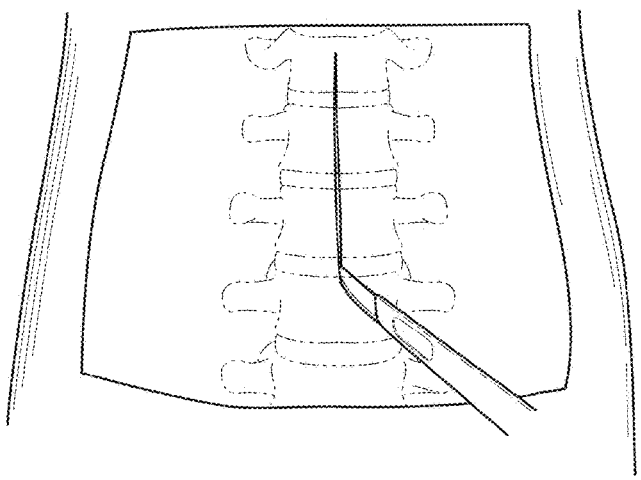
FIG. 12 depicts an incision in the area depicted in FIG. 11.
Figure 13:
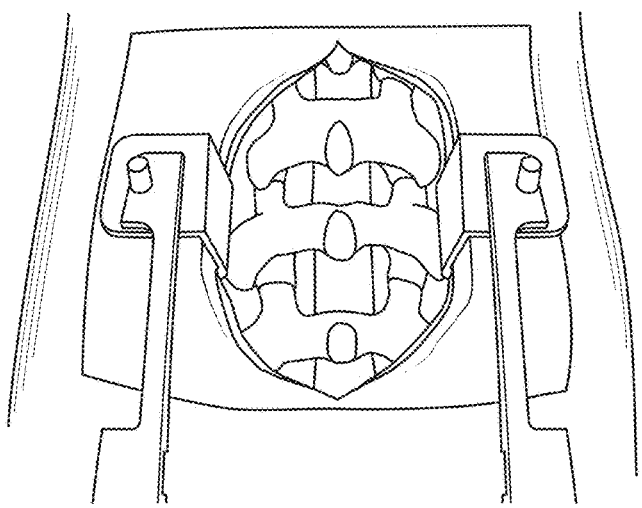
FIG. 13 depicts the area around the incision being resected to allow access to the area of the spine where insertion of a delivery system according to the present invention will take place.

As shown in FIG. 11, a patient will be positioned to provide access to the patient's back, such as for a laminotomy. A cut will be made along the length of the spine (FIG. 12), and the area will be resected to provide access to the spinal area (FIG. 13). The expandable member will then be inserted into the resected area, posteriorly to anteriorly until a desired placement and position is found so that the expandable member 14 can be properly inflated.

Figure 14:
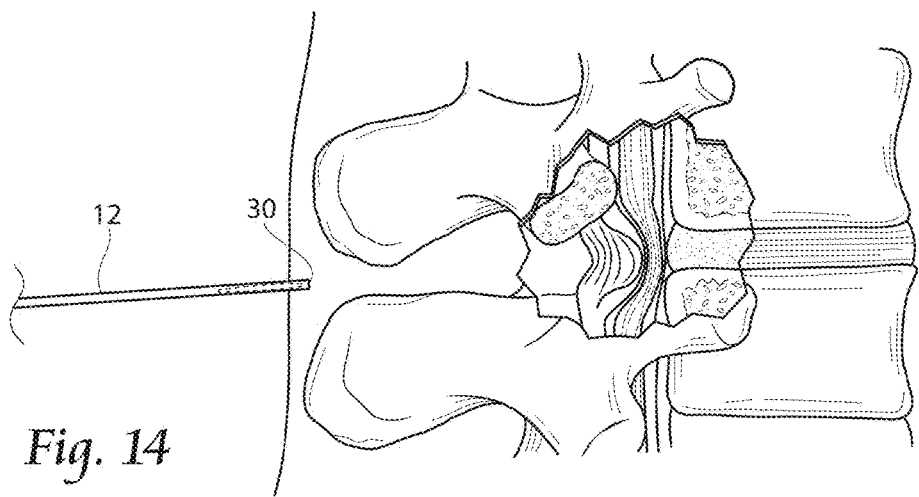
FIG. 14 is a partially cut-away view of the spinal region as shown in FIG. 6A showing the first position of the delivery system near the spinal region.
Figure 15:
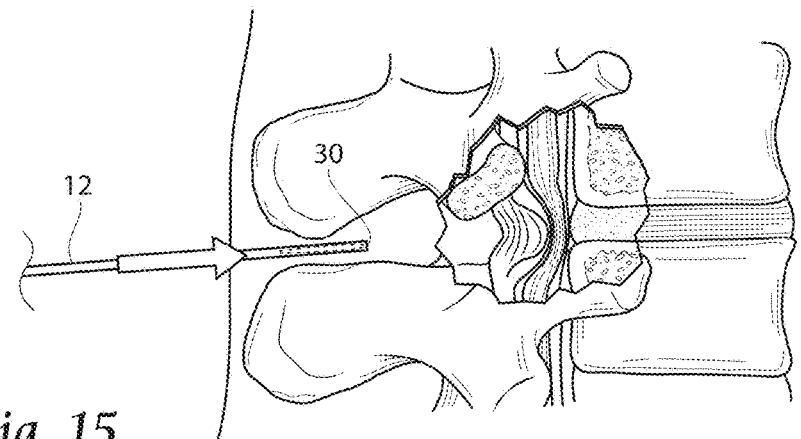
FIG. 15 depicts a further step in advancing the delivery system into the spinal area.
Figure 16:
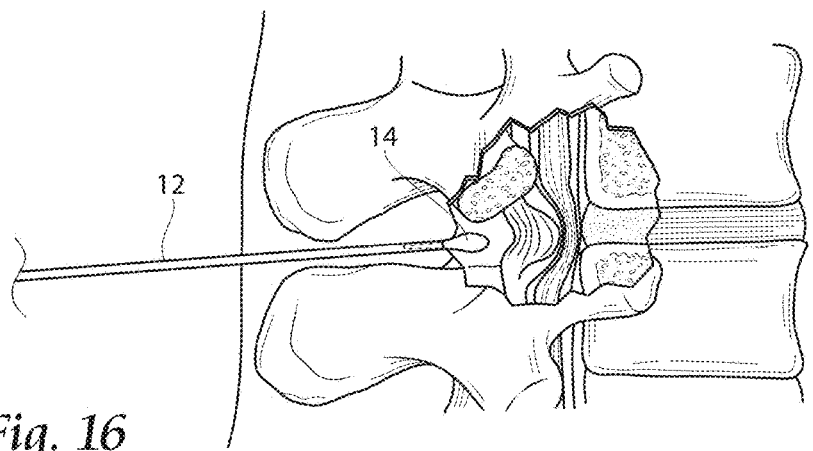
FIG. 16 depicts another further step in advancing the delivery system in to the spinal area to be treated, with the inflatable member being slightly expanded.

FIG. 14 shows an initial positioning of the catheter 12 as it is introduced posteriorly through the laminotomy site. The tip 30 of the catheter 12 is positioned at the beginning of the subarticular zone. The catheter 12 will be slowly moved forwardly in a posterior to anterior direction, further into the foramen (FIG. 15), wherein the expandable member 14 is slowly inflated (FIG. 16). As previously discussed, the positioning of the expandable member 14 will be monitored by the use of a marker, such as a fluoroscopic or echogenic marker.

Figure 17:
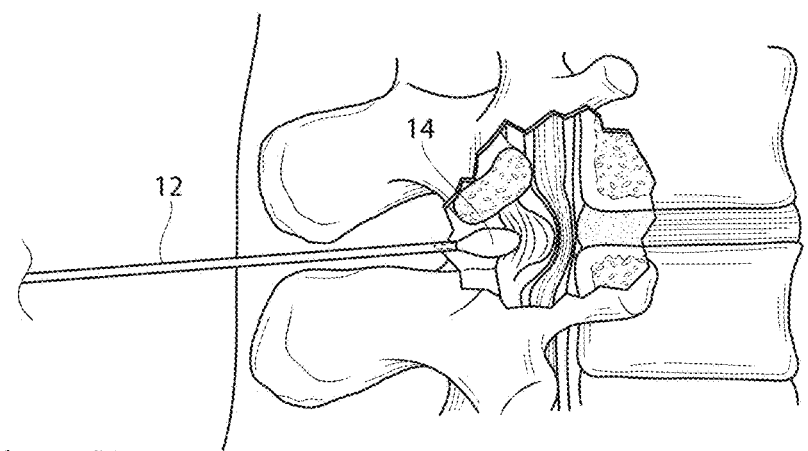
FIG. 17 depicts another further step in advancing the delivery system into the spinal area to be treated.
Figure 18:
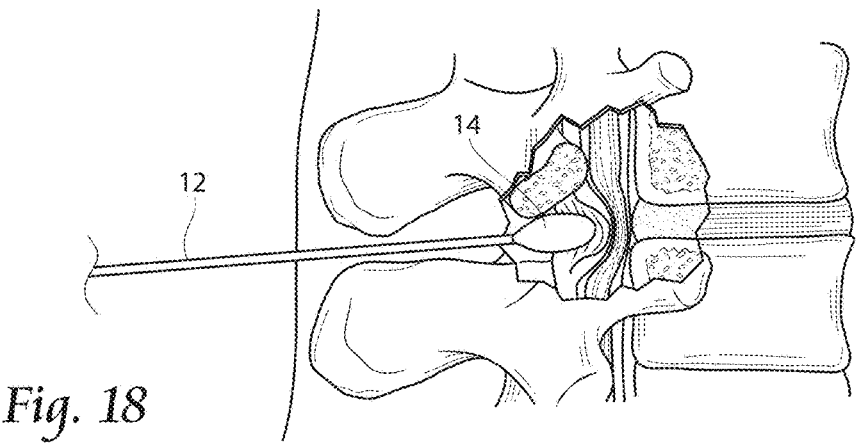
FIG. 18 depicts the delivery system being positioned as desired within the spinal area.

Once the catheter 12 and the expandable member 14 are determined to be in a safe position, the catheter 12 may be further inserted into the foramen, with the expandable member being further inflated (FIGS. 17 and 18). The process of insertion and inflation will be repeated until the surgeon has determined that the expandable member is properly positioned. Further, if it is determined that the expandable 14 member may not be properly inflated or positioned after any particular step, the catheter 12 can be retracted and/or the expandable member 14 can be partially deflated to reposition the catheter 12 and the expandable member 14. In this manner, the stepped process will do minimal agitation or discomfort to the patient while carrying out the process.

Figure 19:
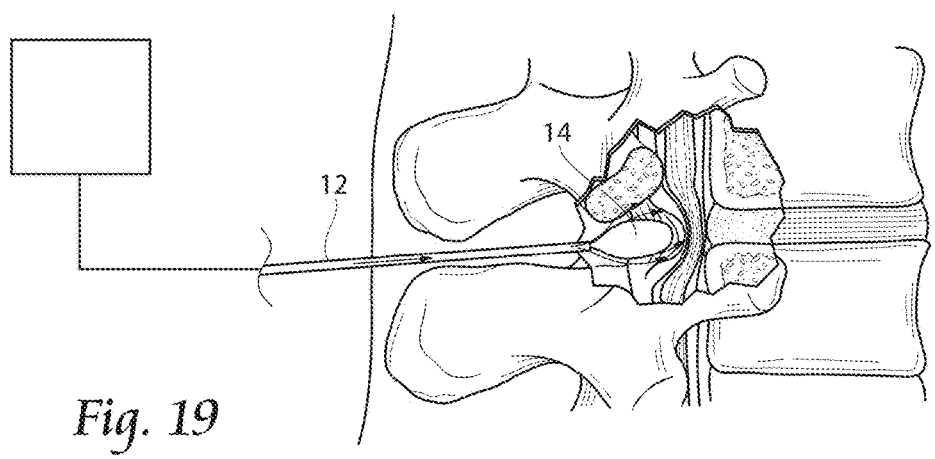
FIG. 19 depicts the delivery of a medicament or other solution to the treated area.

If necessary, a medicinal or therapeutic material such as anesthetics, steroids, growth factors, stem cell material, or other materials, may be injected through the system into the treated foraminal space, as demonstrated in FIG. 19. As shown, the materials are injected using the same catheter 12 as that which delivered the expandable member 14. However, it may be possible that a second catheter dedicated to the delivery of these materials may also be employed.

Figure 20:
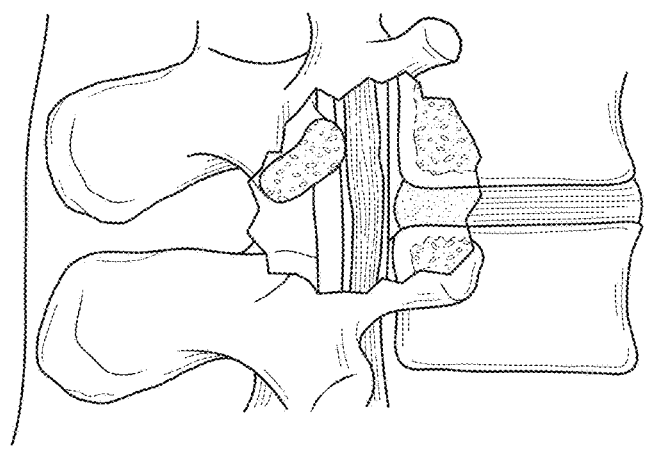
FIG. 20 demonstrates the spinal stenosis being treated, with the inflatable member being retained in place.

Once treatment and process has been carried out, the expandable member 14 and the catheter 12 can be removed, as shown in FIG. 20. The impingement on the thecal sac and/or the spinal cord has been removed/minimized, thereby treating the stenosis.

The process described can also be carried out from different angles and positions within the vertebral region.

Figure 21:
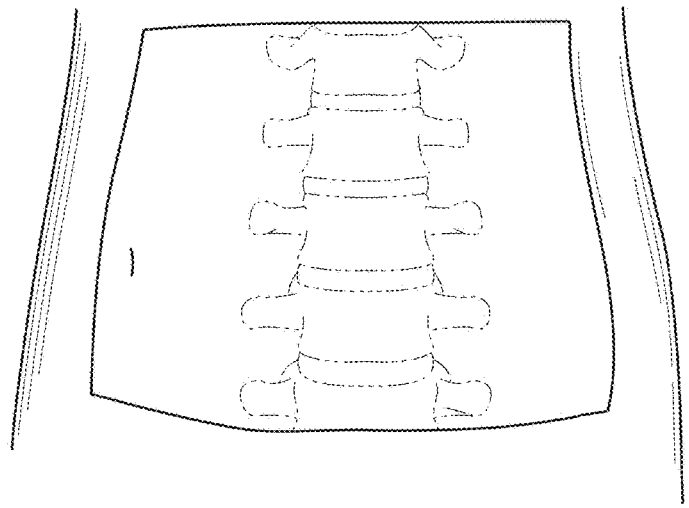
FIGS. 21-29 demonstrate a similar process as described above, with the exception that the delivery device will enter the spinal area from a different position.
Figure 22:
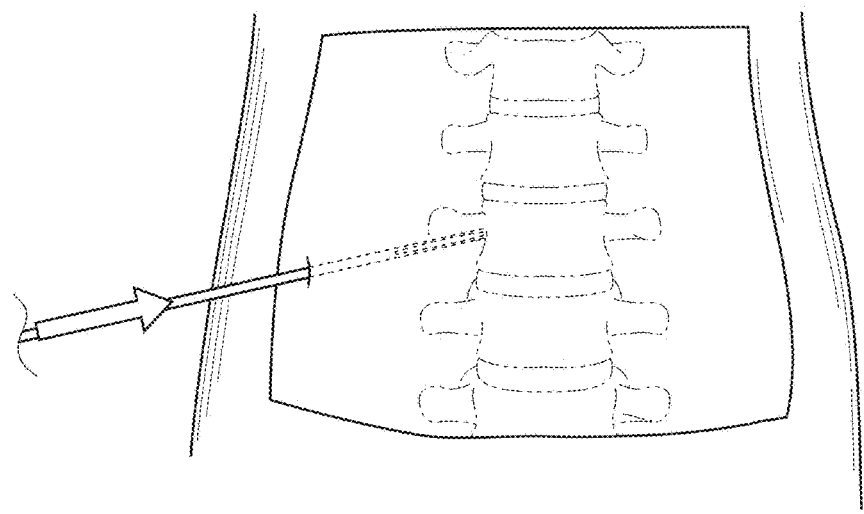
Figure 23:
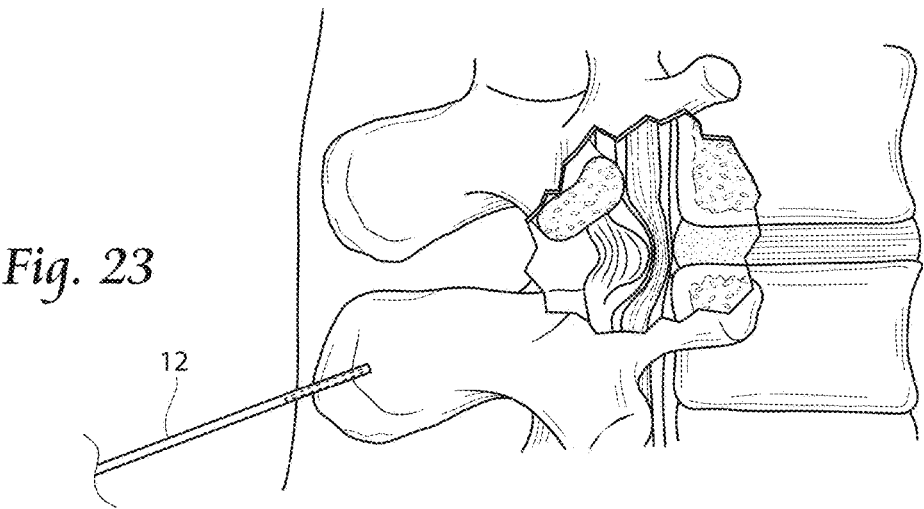

For example, FIGS. 21-29 depict another embodiment of the process of the present invention, wherein the stenosis is approached percutaneously. As shown in FIG. 21, an incision is made laterally from where the vertebral area where the stenosis is located. The catheter 12 and the expandable member 14' will then be inserted laterally to medially, as demonstrated in FIG. 22.

As with the previously described method, the catheter will be positioned in a safe area at the initial steps of the process. In this instance, the catheter 12 will be positioned near the superior articular process, in an area referred to as Kambin's triangle (i.e. the Safe Triangle) (also see FIG. 4).

Figure 24:
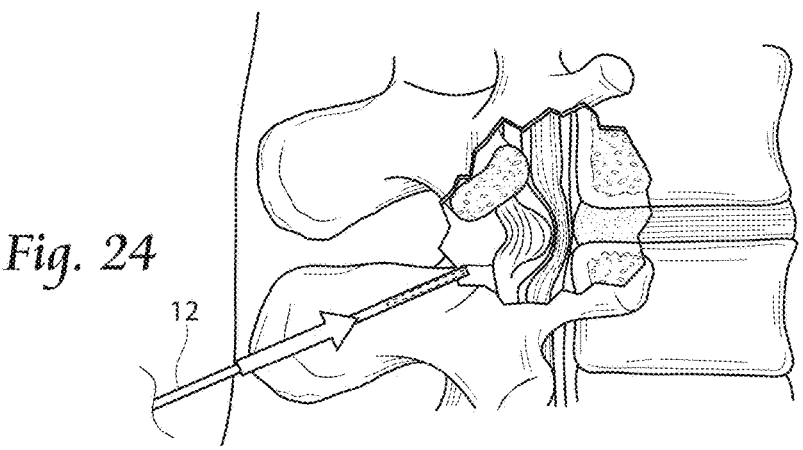
Figure 25:
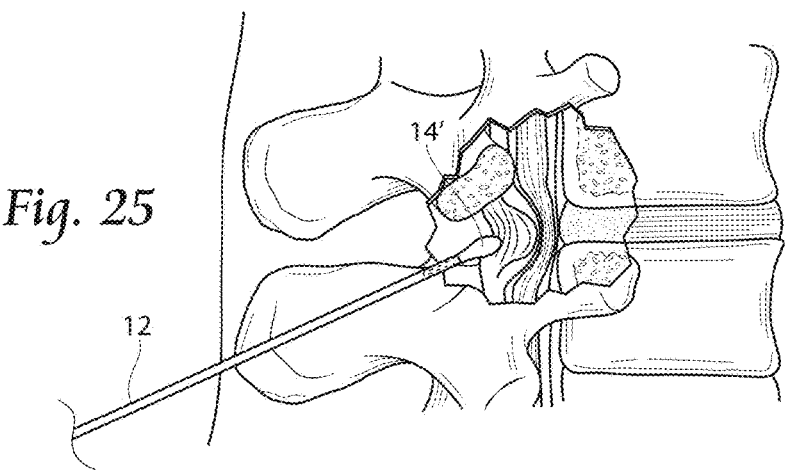

Once properly positioned, the catheter 12 can be advanced medially, as shown in FIG. 24. If the further position is determined acceptable, the expandable member 14' can be slowly inflated (FIG. 25). Monitoring of the position of the catheter 12 and expandable member 14' can be carried out by the use of a marker, such as a fluoroscopic or echogenic marker 28, as previously described.

The steps of insertion and inflation can be repeated (see FIGS. 26 and 27) as many times as necessary until the expandable member 14' is properly positioned. The process of insertion and inflation will be repeated until the surgeon has determined that the expandable member 14' is properly positioned. And, as previously discussed, if it is determined that the expandable member 14' may not be properly inflated or positioned after any particular step, the catheter 12 can be retracted and/or the expandable member 14' can be partially deflated to reposition the catheter 12 and the expandable member 14'. In this manner, the stepped process will do minimal agitation or discomfort to the patient while carrying out the process.

Figure 28:
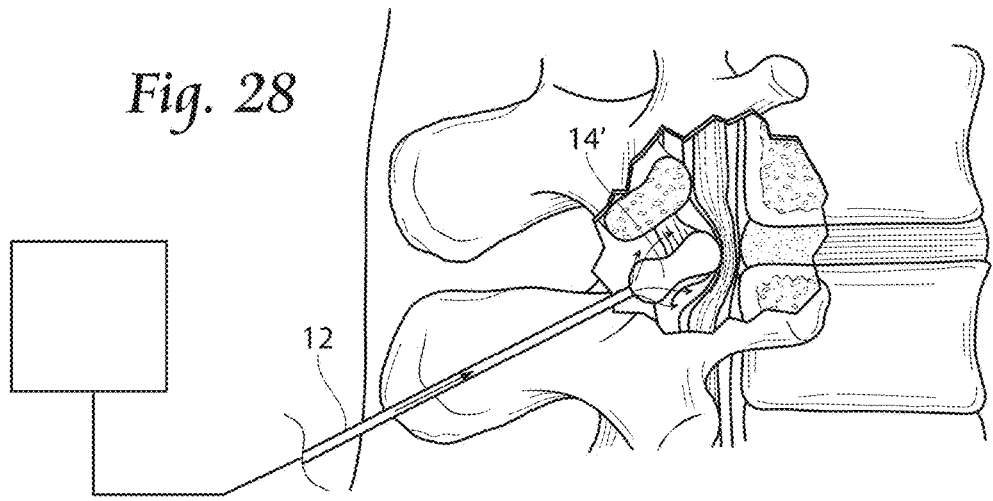

If necessary, a medicinal or therapeutic material such as anesthetics, steroids, growth factors, stem cell material, or other materials, may be injected through the system into the treated foraminal space, as demonstrated in FIG. 28. As shown, the materials are injected using the same catheter 12 as that which delivered the expandable member 14'. However, it may be possible that a second catheter dedicated to the delivery of these materials may also be employed.

Figure 29:
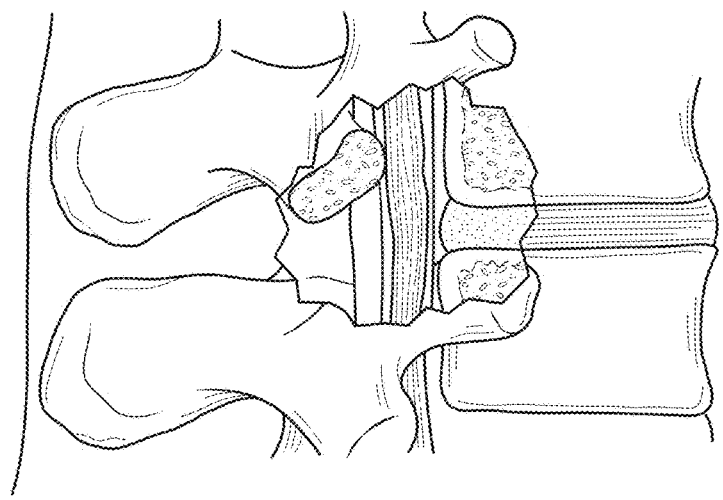

Once treatment and process has been carried out, the expandable member 14' and the catheter 12 can be removed, as shown in FIG. 29. The impingement on the thecal sac and/or the spinal cord has been removed/minimized, thereby treating the stenosis.

Figure 26:
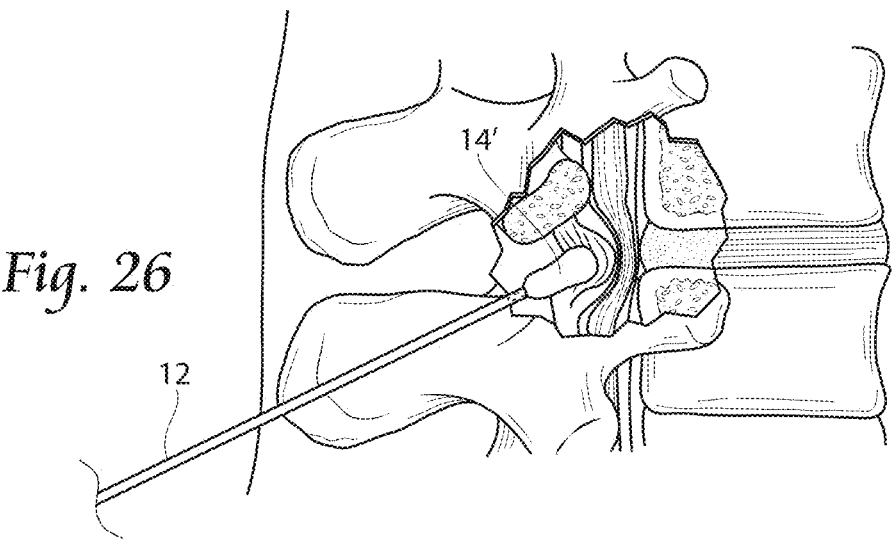
Figure 27:
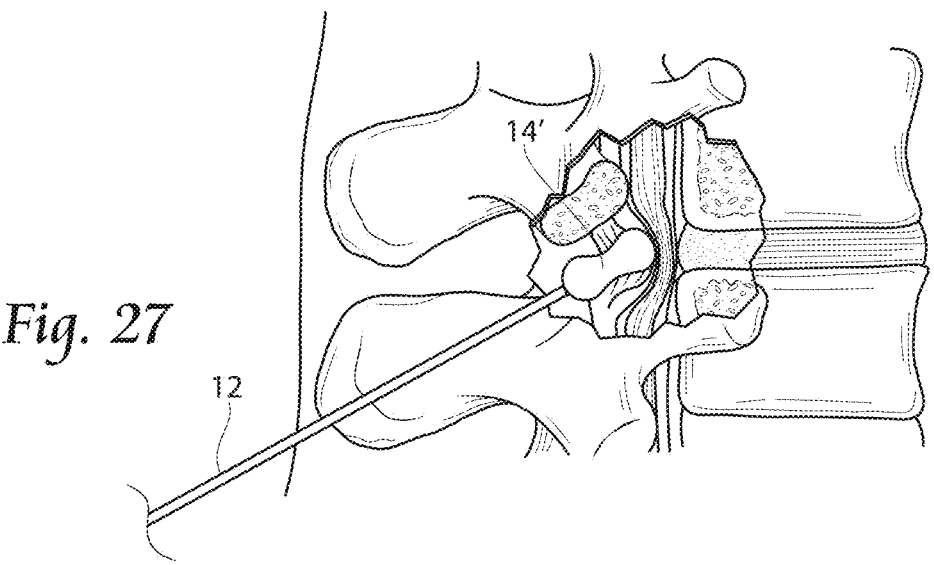

As shown in FIGS. 26-28, the expandable member 14' is of a dumbbell-shape, as previously discussed as one possible shape for the expandable member. The expandable member will act as an anchor between the medial and lateral sides of the facet joint, thereby minimizing the risk of the expandable member 14' being displaced into the medial canal, thereby potentially avoiding the risk of dural injury, or displacing laterally, thereby preventing dislodging of the balloon (expandable member 14') laterally and out of the foramen.

As appreciated and understood with such procedures as described herein, there are different layers, e.g. skin and fascia (deep thick layer underneath the skin), that need to be navigated when performing such a procedure. Likewise, the present devices and procedures are used around sensitive nerves and the foramen. The devices and methods of the present invention are designed to be used in such differing areas of the body. For example, to penetrate the skin and the fascia, a sharp device may be desired to penetrate these layers, while a more blunt device may be desirous when navigating around the nerves and the foramen. The delivery device and system 100 shown in FIG. 30 contemplates such considerations.

Figure 30:
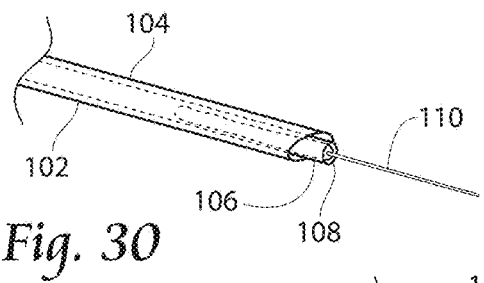
FIG. 30 depicts a perspective partially cut-away view of an alternate delivery device of the present invention.

The delivery device 100 of FIG. 30 generally comprises a catheter 102. The delivery device 100 comprises a pair of stylets 104 and 106 that will be used to for navigation of the delivery device through the various layers discusses above. The delivery device also houses an inflatable member 108, and preferably a guide wire 110 to assist in properly positioning the inflatable member in place.

Figure 31:
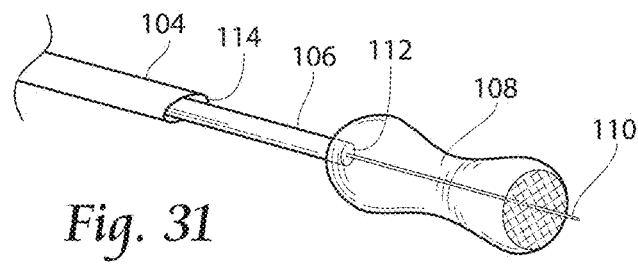
FIG. 31 depicts the device of FIG. 30 with the inflatable member in an inflated position.

As shown in FIG. 31, the stylets 104 and 106 of the delivery device 100 are telescopingly arranged with one another. The interior stylet 106 has a blunt end 112, which is beneficial when navigating around the foramen and nerves located in the spinal area. The blunt end 112 of the interior stylet 106 will also minimize any damage, e.g. puncturing, of the inflatable member 108. The inflatable member 108 shown in FIG. 31 is dumb-bell shaped, but, as discussed above, a spherical or other shaped balloon may be used, as noted with inflatable members 14, 14'.

The exterior stylet 104 has an angled or sharpened end 114, which assists in piercing or penetrating the skin and the fascia. For example, the beveled end 114 of the exterior stylet 104 may have an angle (greater than 0°), e.g. 20° or 30°, that will provide the sharpened edge. To protect the inflatable member 108 from being damaged by the exterior stylet 104, the inflatable member 108 is preferably located within the interior stylet 106, thereby providing a barrier between the exterior stylet 104 and the inflatable member 108.

Figure 32:
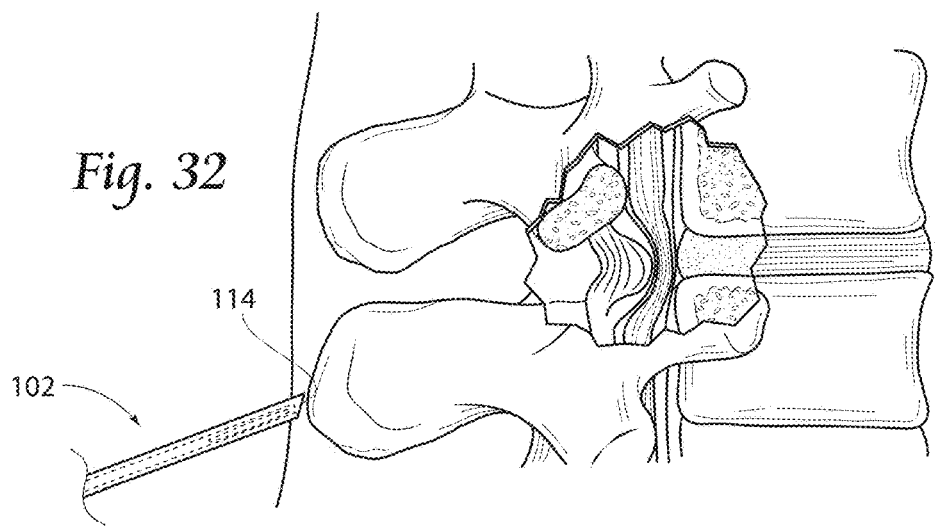
FIGS. 32-39 demonstrate a similar process as the process described in FIGS. 21-29, using a delivery device as shown in FIG. 30.

FIG. 32 demonstrates a step in the insertion of the delivery device into a patient. The patient will be initially prepped, as shown previously in FIGS. 21 and 22. Once prepped, the catheter 102 will be positioned in a safe area. The catheter 102 will be positioned near the superior articular process, in an area referred to as Kambin's triangle (i.e. the Safe Triangle) (also see FIG. 4). The sharpened end 114 of the exterior stylet 104 will be used to penetrate the skin and the fascia.

Figure 33:
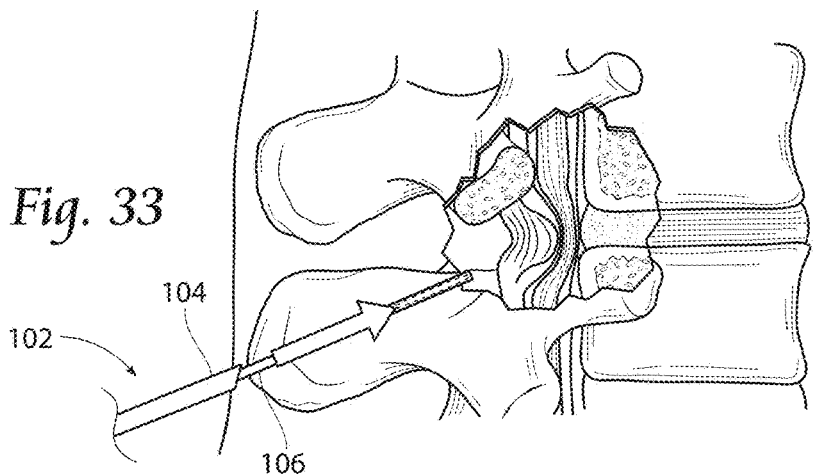
Figure 34:
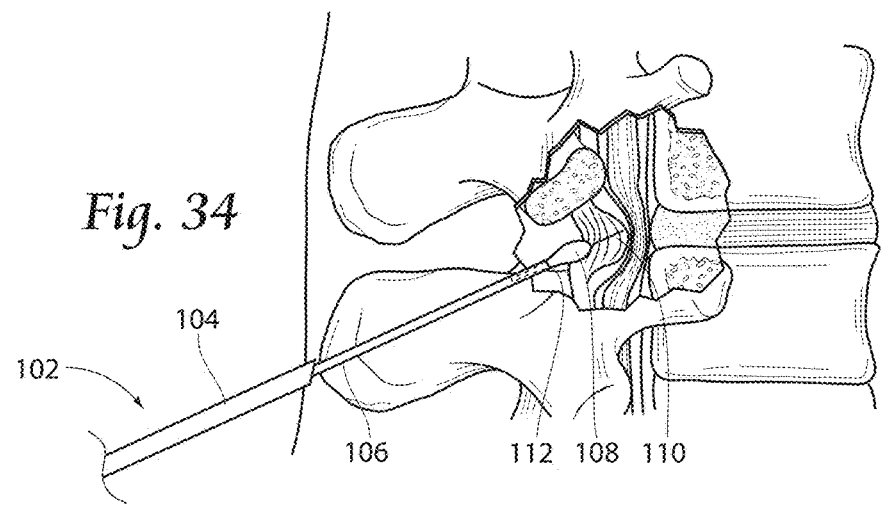

Once properly positioned and the exterior stylet 104 has properly and sufficiently pierced and penetrated the skin and the fascia, the interior stylet 106 will be extended, as shown in FIG. 33, with the exterior stylet 104 being maintained at the initial position shown in FIG. 32. Once properly positioned in an acceptable position, the inflatable member 108 will then be further extended outwardly from the blunt 112 end of the interior stylet 106 (FIG. 34), and the inflation process can commence, with the process being monitored, as previously described. The guide wire 110 will be used in properly navigating the inflatable member into the proper positioning.

Figure 35:
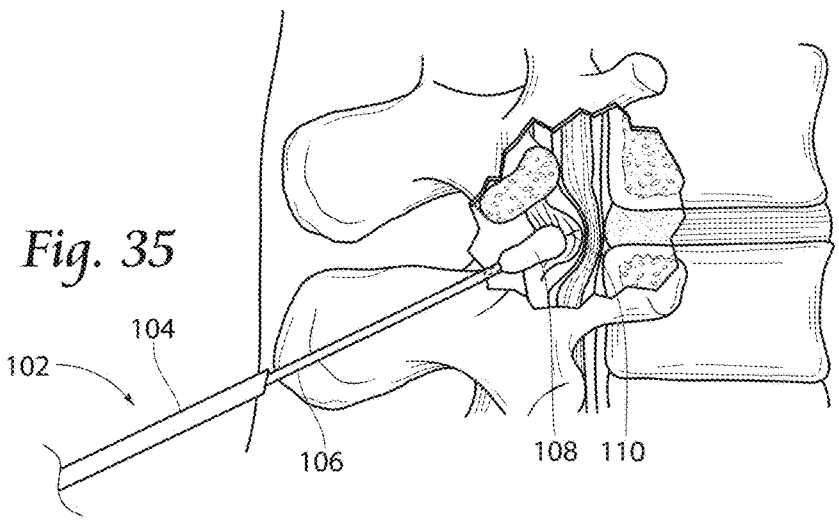
Figure 36:
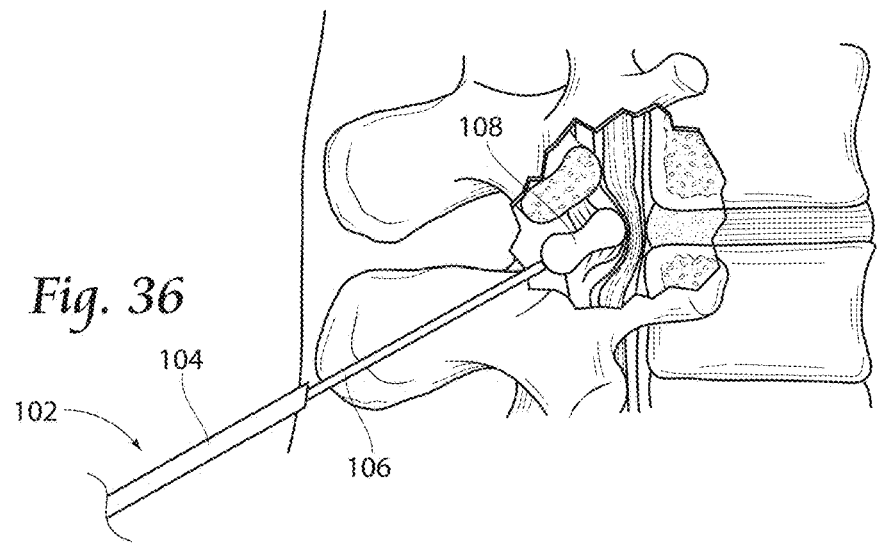

As previously described above, the steps of insertion and inflation can be repeated as many times as necessary (see FIGS. 35 and 36). The process of insertion and inflation will be repeated until the surgeon has determined that the expandable member 108 is properly positioned. And, as previously discussed, if it is determined that the expandable member 108 may not be properly inflated or positioned after any particular step, the catheter 102 can be retracted and/or the expandable member 108 can be partially deflated to reposition the catheter 102 and the expandable member 108. In this manner, the stepped process will do minimal agitation or discomfort to the patient while carrying out the process. Once properly positioned, the guide wire 110 is withdrawn from the device (FIG. 35). As previously noted with respect to FIG. 8, the guide wire 110 may be removed by unscrewing the guide wire from the delivery device.

Figure 37:
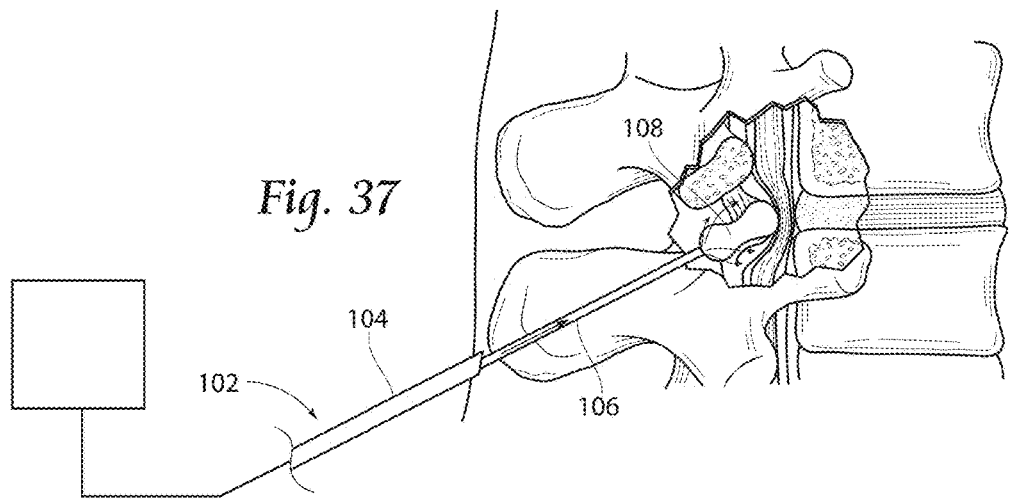

If necessary, a medicinal or therapeutic material such as anesthetics, steroids, growth factors, stem cell material, or other materials, may be injected through the system into the treated foraminal space, as demonstrated in FIG. 37. As shown, the materials are injected using the same catheter 102 as that which delivered the expandable member. However, it may be possible that a second catheter dedicated to the delivery of these materials may also be employed.

Figure 38:
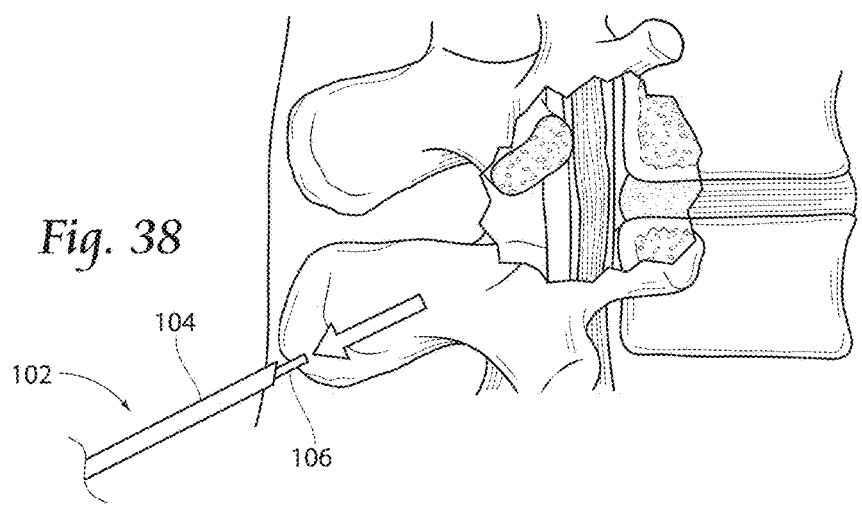
Figure 39:
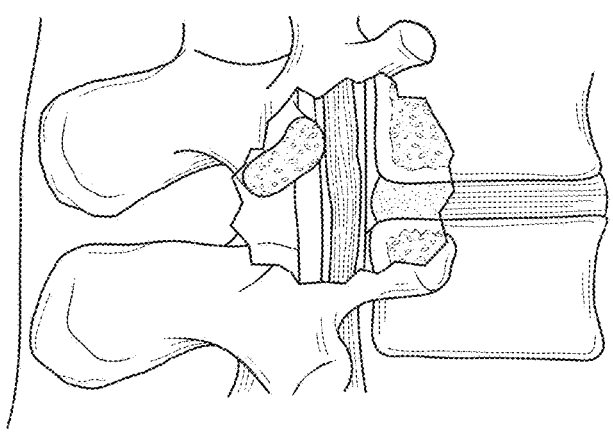

Once treatment and process has been carried out, the expandable member 108 and the catheter 102 can be removed, as shown in FIG. 38, with the inflatable member 108 being retracted into the interior stylet 106. The interior stylet 106 is then telescoped inside of the exterior stylet 104, and the catheter 102 can be removed. The impingement on the thecal sac and/or the spinal cord has been removed/minimized, thereby treating the stenosis.

Figure 40:
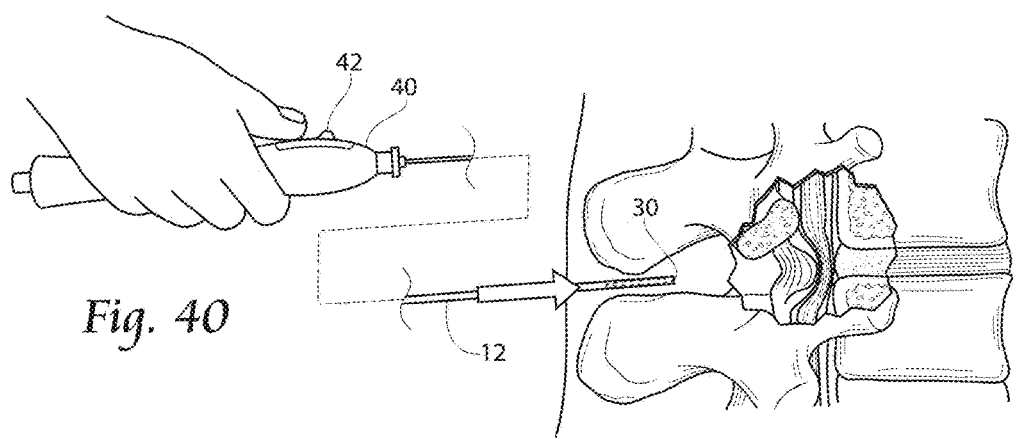
FIG. 40 demonstrates a process similar to the processes described in FIGS. 21-39, with the delivery system being housed in a portable device.
Figure 43:
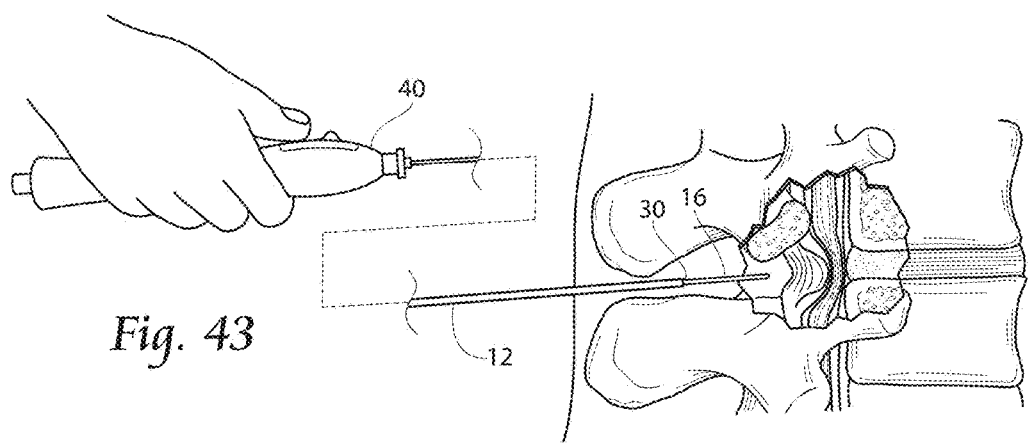
FIG. 43 demonstrates a further step in the process of FIG. 42, wherein the guide wire is retracted from the spinal area.

The system and device can delivered in a similar fashion as described in the methods above, but with the delivery system being positioned within a portable housing 40. The portable housing is preferably designed so that it can be hand held. As shown in FIG. 40, the portable housing 40 allows deployment of a catheter, in the similar fashion as described above. The portable housing preferably has a switch or control device 42 that assists in delivery of the guide wire 16 and/or the inflatable member 14' (see FIG. 43). The control device 42 may comprise further devices so that the individual parts of the system, e.g. the guide wire 16 or the inflatable member 14' could be individually controlled. The control device can be used to monitor the volume, e.g. mm³, of the inflatable member 14', so that the inflatable member 14' will be properly inflated.

Figure 41:
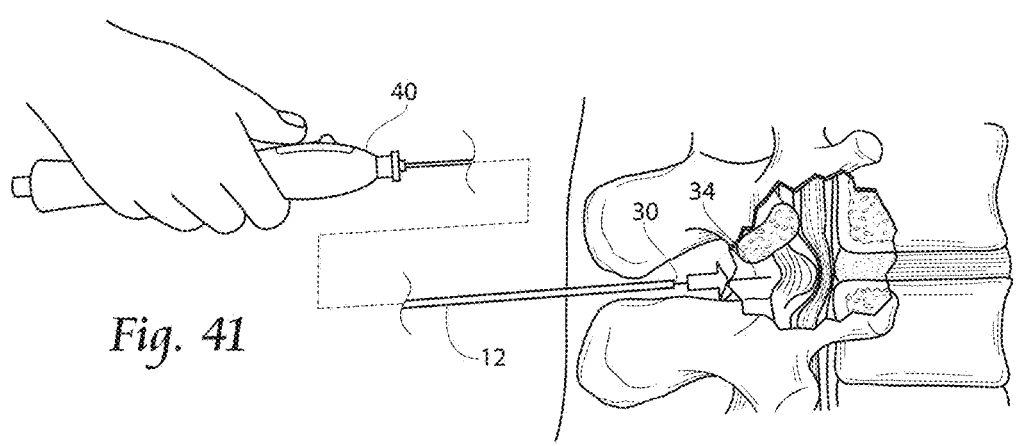
FIG. 41 demonstrates a further step in the process shown in FIG. 40, wherein a guide wire is inserted into the spinal area.
Figure 42:
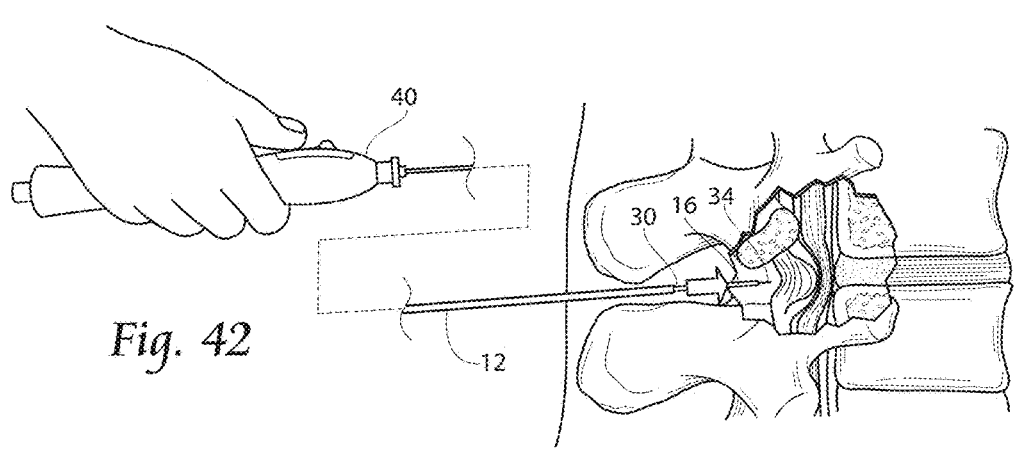
FIG. 42 demonstrates a further step in the process of FIG. 41, wherein a catheter is inserted into the spinal area.

FIG. 40 shows the catheter 12 being properly positioned in the spinal area, as described above. Once the catheter is positioned, the guide wire 16 can be introduced into the spinal area, as demonstrated in FIG. 41. Once the guide wire 16 is positioned, the cannula 15 that will deliver the inflatable member 14' is introduced into the spinal area (FIG. 42).

Figure 44:
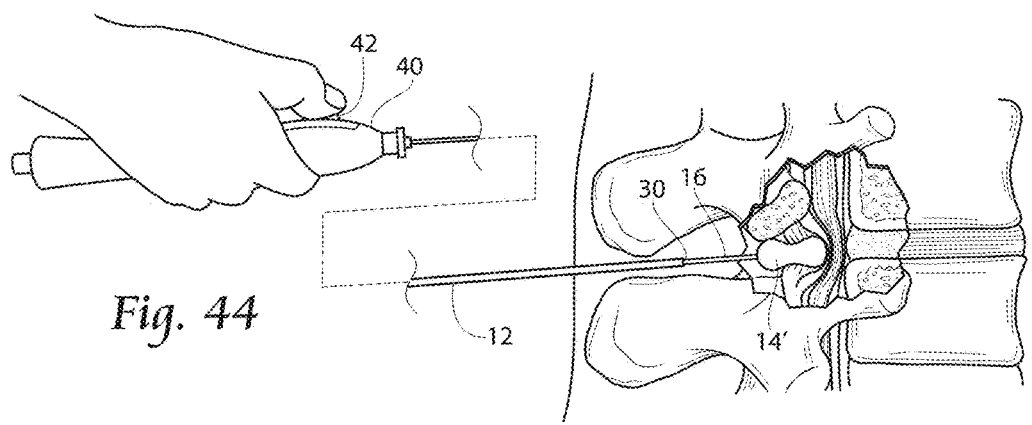
FIG. 44 demonstrates a further step in the process of FIG. 43, wherein an inflatable member is deployed in the spinal area.
Figure 45:
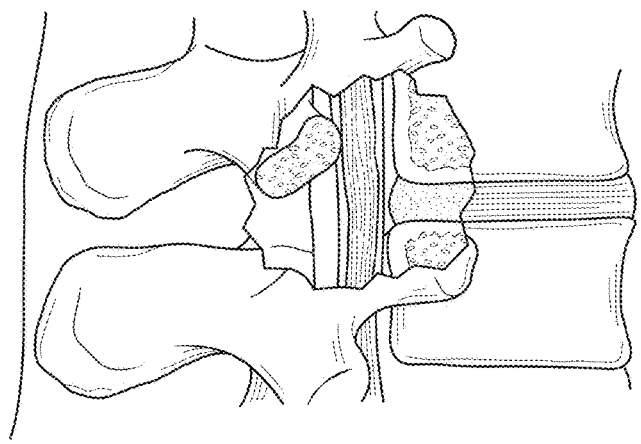
FIG. 45 demonstrates the spinal stenosis being treated, with the inflatable member being removed from the spinal area.

As an alternate step to the processes discussed above, the guide wire 16 is then removed from the spinal area (FIG. 43), prior to the deployment of the inflatable member 14' (FIG. 44). It is understood, as described above, that the inflatable member can be deployed and retracted as necessary so that the device can be properly positioned to treat the stenosis (see FIG. 45).

Figure 46:
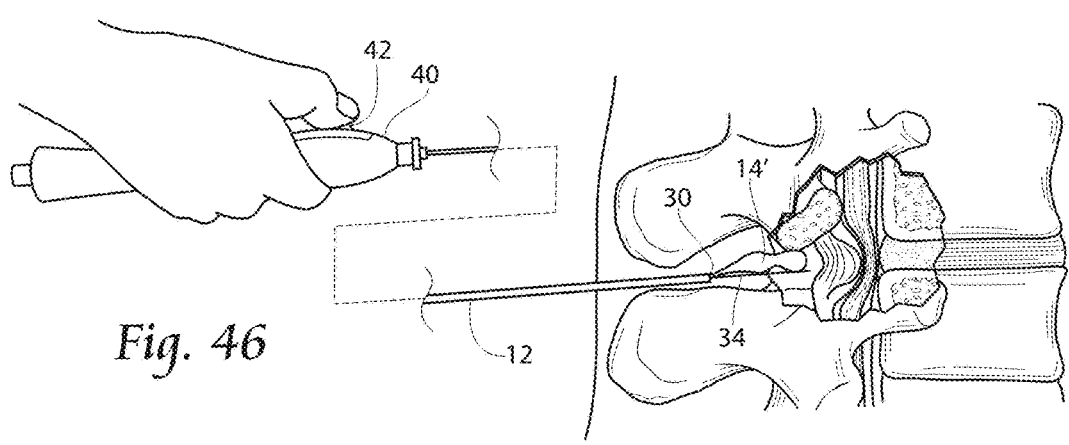
FIG. 46 demonstrates an alternate delivery method of the delivery system, wherein the inflatable member is delivered alongside of the guide wire.

It should be understood that either expandable member shape, or other shapes, could be used with either of the processes described. Provided that an expandable member was inserted and progressed as described, it is understood that the process will be covered by the present disclosure. For example, FIG. 46 demonstrates a delivery step that could be used in any of the above procedures. The inflatable member 14' is delivered over the guide wire 16, but is used with a portable housing 40, as shown in FIG. 40.

As is understood from the above embodiments, the present inventions are designed to provide less invasive surgical procedures compared to prior art systems and methods. The following figures further demonstrate the ability of the present invention to be manipulated and worked in the spinal area in a concise fashion.

Figure 47:
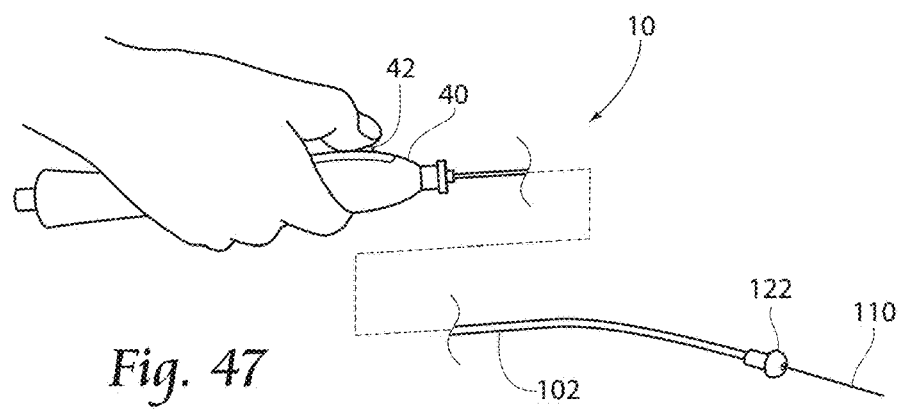
FIG. 47 further demonstrates a partially cut-away view of a further arrangement of a delivery system according to the present invention.
Figure 51:
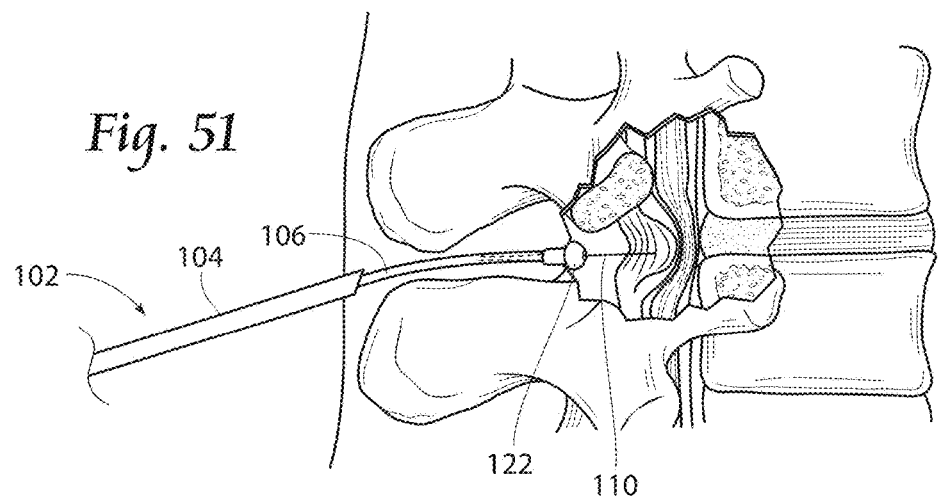
FIG. 51 is a partially cut-away view of the spinal region as shown in FIG. 6A showing the first position of the delivery system depicted in FIG. 47 near the spinal region.

FIG. 47 shows the portable housing 40, which allows deployment of a catheter 102, in the similar fashion as described above. The portable housing 40 preferably has a switch or control device 42 that assists in delivery of the guide wire 110 and/or the inflatable member 108 (see FIGS. 51 and 52). The portable housing will also be able to deploy inserts 120, (see FIGS. 53 and 54), which will be described in further detail, below.

Referring again to FIG. 47, the system 10 incorporates two features that will further allow the system 10 to operate within the spinal area: a bendable catheter 102 and guide wire 110, as well as having a tip 122 to the guide wire 110 that is ball-shaped or another curved shape. The bendable features allow for better navigation through the spinal are and better navigation in the deep tissue surrounding the spine.

Figure 48A:
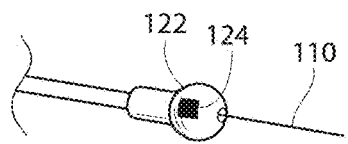
FIGS. 48A-48C depict alternate arrangements for a guide member used in the systems and methods of the present invention.
Figure 48B:
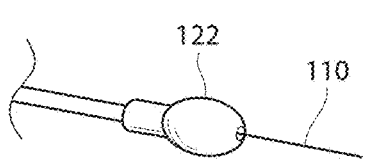
Figure 48C:
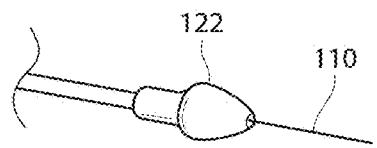

FIGS. 48A-48C depict various tips 122 that could be incorporated into the system. FIG. 48A shows a ball-shaped guide tip 122, while FIG. 48B shows a more oval-shaped tip, with FIG. 48C providing a more conical-shaped tip. Depending on the particular patient and the particular surgeon, any of these arrangements may be used in the present invention to allows a safe approach into the neroforaminal canal. FIG. 48A also shows a radio-opaque 124 marker that will make for easy visualization under x-ray and localization. The radio opaque marked 124 could be incorporated into any of the tips 122.

Figure 49A:
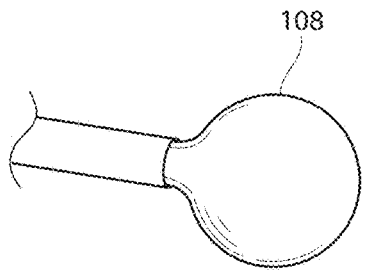
FIGS. 49A-49B inflatable members used in the systems and methods of the present invention.
Figure 49B:
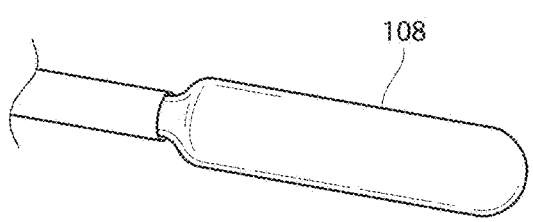

Referring to FIGS. 49A and 49B, it is contemplated that the inflatable member 108 could be cannutaled, meaning that it would be able to slip over the ball-tipped or other curved shaped guide tip 122 when the guide tip is positions at the appropriate location in the neuroforamen. As previously discussed, the inflatable members 108 could be of varying diameters and lengths (see FIGS. 49A and 49B), depending on the particular spinal area being treated, as well as the severity of the stenosis being treated. For example, a smaller diameter of ball-tipped guide for cervical or thoracic areas. This will be discussed further below.

Figure 50A:
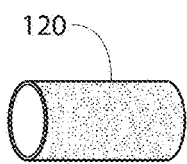
FIGS. 50A-50C demonstrate various inserts that can be used with the systems and methods of the present invention.
Figure 50B:
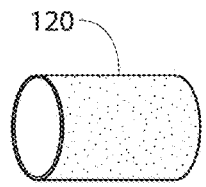
Figure 50C:
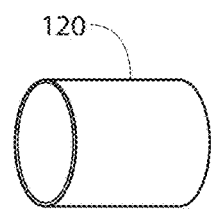

As noted above, the system 10 may also be capable of delivering inserts 120 into the foramen, which can assist in slowly and safely decompressing the foraminal stensosis. FIGS. 50A-50C depict different inserts 120 that can be used in the present invention. The inserts 120 are generally thin, elongated inserts, which will have varying degrees of coarseness on the outside of the insert. For example, FIG. 50A depicts a thin insert 120, having a rather coarse outer surface, while FIG. 50C depicts an insert 120 having a larger diameter and having a smooth surface. The use of the size and coarseness of the insert 120 maybe modified depending on the severity of the stenosis.

As shown below, the use of varying sizes of inflatable members and inserts are used if severe stenosis does not allow for the ball-tipped guide tip to go in the neuroforamen. The guide tip is placed at the outer edge of the foramen, and the smaller inserts may be used sequentially to open the foramen, allow for sequential advancement of the guide. Then deploy appropriate thin inserts, or balloon insert, to open the severe stenosis, then the stylet is removed and contrast is injected to assess the degree of stenosis improvement by evaluating medial uptake of contrast in the epidural space. Then deploy the inflatable member 14, e.g. a "sliding cannulated balloon" over the ball-tipped guide 122, to decompress the foraminal stenosis. The steps may be repeated to continue to improve opening the stenosis.

If neuroforaminal stenosis is severe or not safely approachable, especially in smaller regions of spine, cervical or thoracic, the ball-tipped guide maybe placed at the junction of foramen, and the facet joint, and the facet joint is approached with the guide. Then same series of steps may be used. This way the stenosis is decompressed indirectly.

Figure 52:
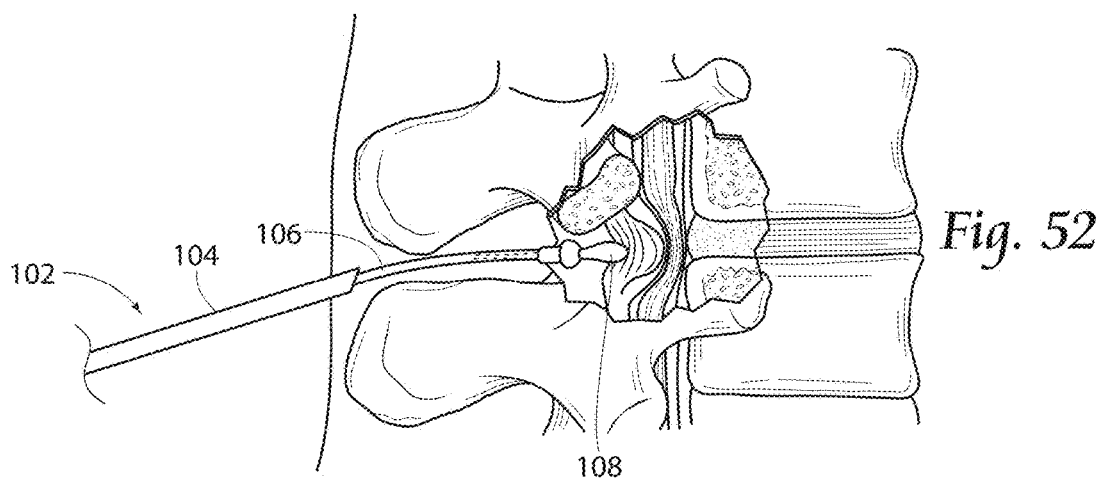
FIG. 52 shows the delivery system depicted in FIG. 51 further deploying an inflatable member into the spinal region.

FIGS. 51-57 demonstrate the method using the inflatable members and inserts discussed directly above above. As shown in FIG. 5, the catheter, stylets 104 and 106 and the guide wire 110 is inserted into the area around the foramen, as discussed above. The curved shape of the stylet 106 and the guide wire 110 assist in entering the area. The guide wire 110 is shown having the ball-shaped guide tip 122. FIG. 52 depicts an inflatable member 14 being inserted into the area, with the inflatable member being inserted over the ball-shaped guide tip 122.

Figure 53:
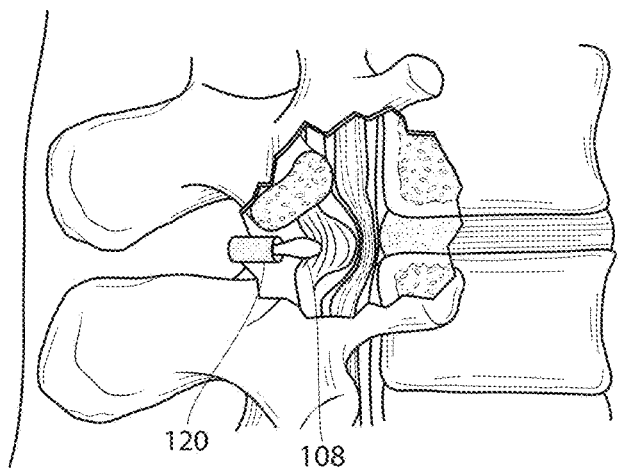
FIG. 53 depicts an insert and the inflatable member of FIG. 53 being deployed into the spinal region.
Figure 54:
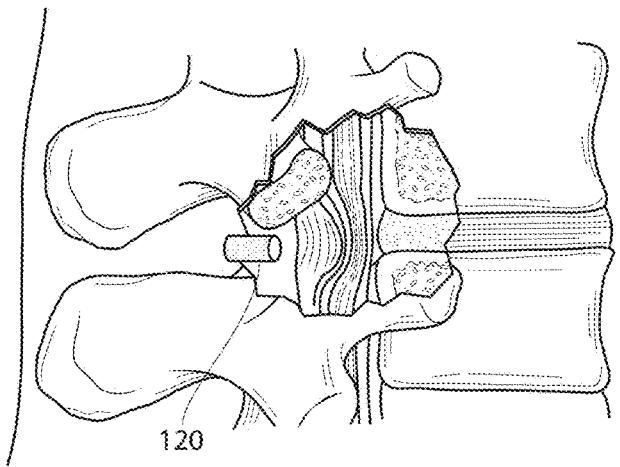
FIG. 54 depicts removal of the inflatable member shown in FIG. 53.

Once the inflatable member 108 is properly positioned, an insert 120 will also be inserted into the area (FIG. 53). As an example, the insert 122 is shown in FIG. 53 as being relatively coarse with a relatively thin diameter. Once the insert 122 is properly positioned, the inflatable member 108 can be removed as noted previously.

Figure 55:
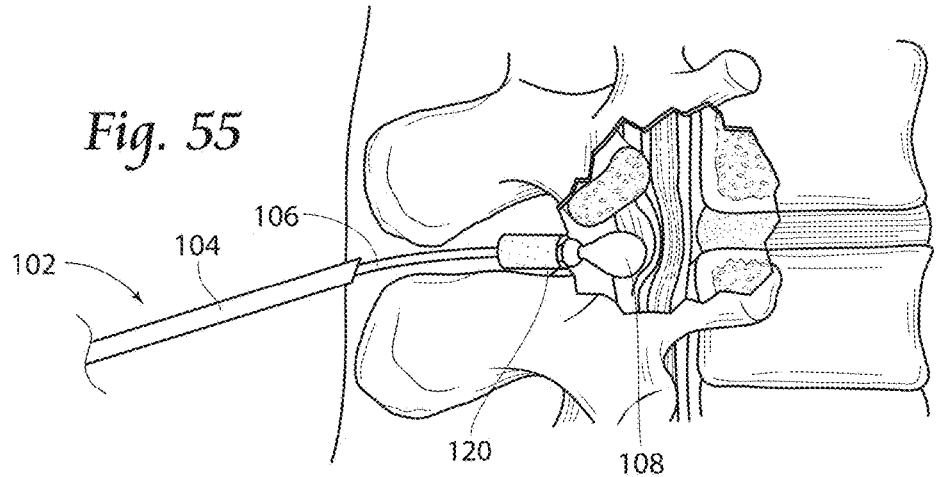
FIG. 55 demonstrates a further inflatable member and insert being inserted into the spinal region.

FIG. 55 demonstrates a further step in the process, wherein another larger inflatable member 108 is inserted, followed by another insert 122, larger in diameter than the previous insert 122.

Figure 56:
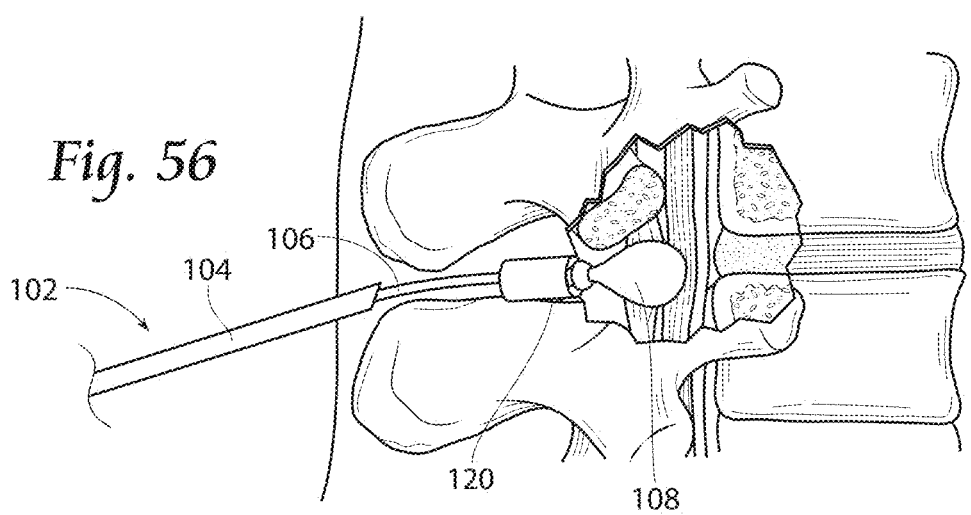
FIG. 56 demonstrates yet another inflatable member and insert being inserted into the spinal region.

FIG. 56 depicts a third set of an inflatable member 108 and an insert 122 being inserted into the area, with the size of each shown in FIG. 56 being larger than the previous size shown (see FIG. 55). The stepped increase of the inflatable members 14 and the inserts 122 helps to minimize the amount of trauma that arises during the procedure.

Figure 57:
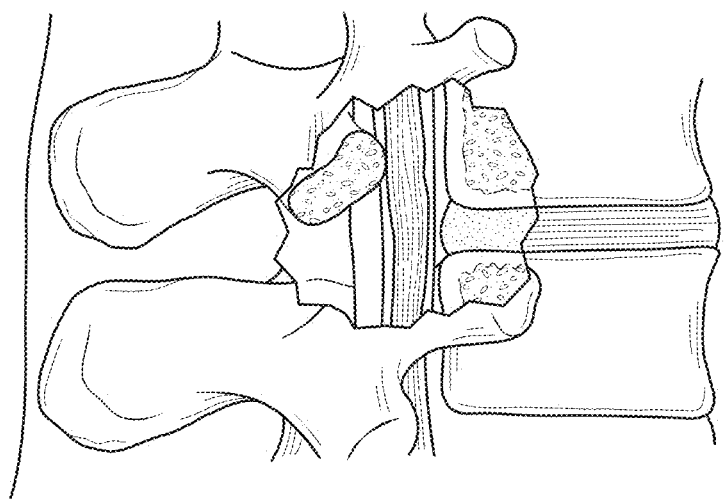
FIG. 57 demonstrates the spinal stenosis being treated, with the inflatable member and insert being removed from the spinal area.

As discussed above, once treatment and process has been carried out, the expandable members 108, inserts 122 and the catheter 12 can be removed, as shown in FIG. 57. The impingement on the thecal sac and/or the spinal cord has been removed/minimized, thereby treating the stenosis.

Figure 58A:
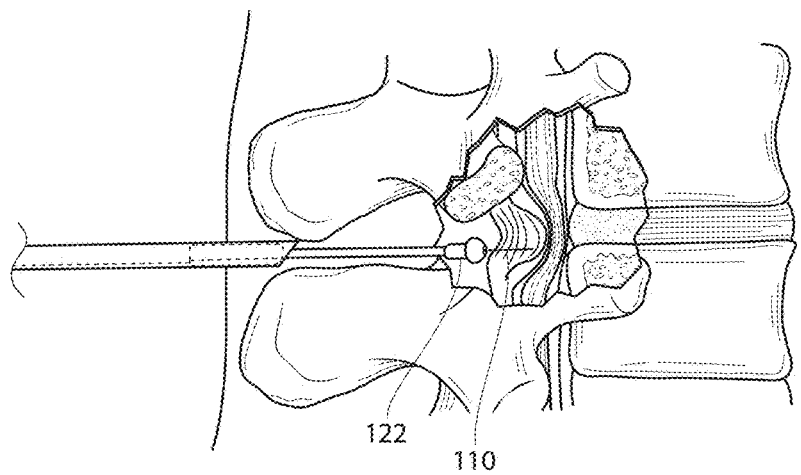
FIGS. 58A-58B demonstrate the use of a further inflatable member and arrangement used in the present systems and methods.
Figure 58B:
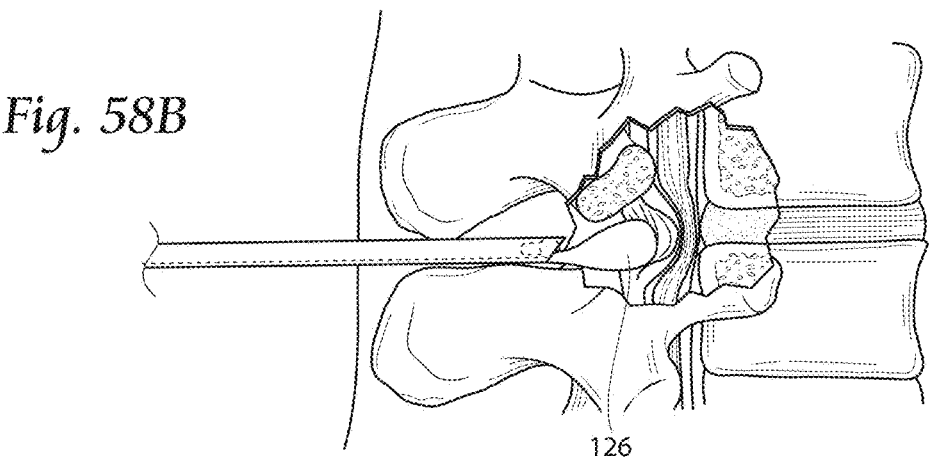

As noted and describe above, the inflatable member 108 can be considered a cannulated sliding balloon 124, which is show in FIG. 58B. The cannulated sliding balloon 124 is slid over the ball-shaped guide tip 122. As demonstrated in FIG. 58A, the catheter 102 and guide wire 110 are inserted between the foramen as previously described. The cannulated sliding balloon 124 will be inserted through the catheter 102 over the ball-shaped guide tip 122. Once the cannulated sliding balloon 126 reaches the guide tip 122, it is inflated and inserted, as shown in FIG. 58B. The ability of the balloon 126 to be inserted over the tip 122 allows for better control where the balloon 126 is being inserted relative to the placement of the tip 122 within the area.

Figure 59:
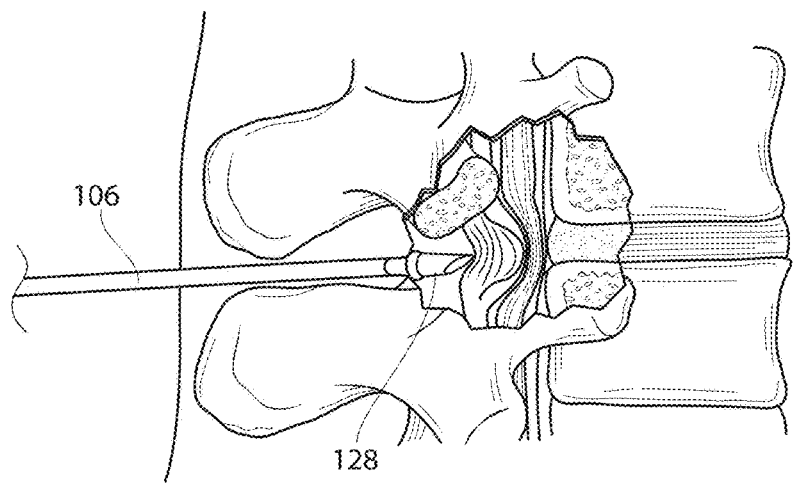
FIGS. 59 and 60 depict further arrangements of stylets used in the delivery systems and methods of the present invention.
Figure 60:
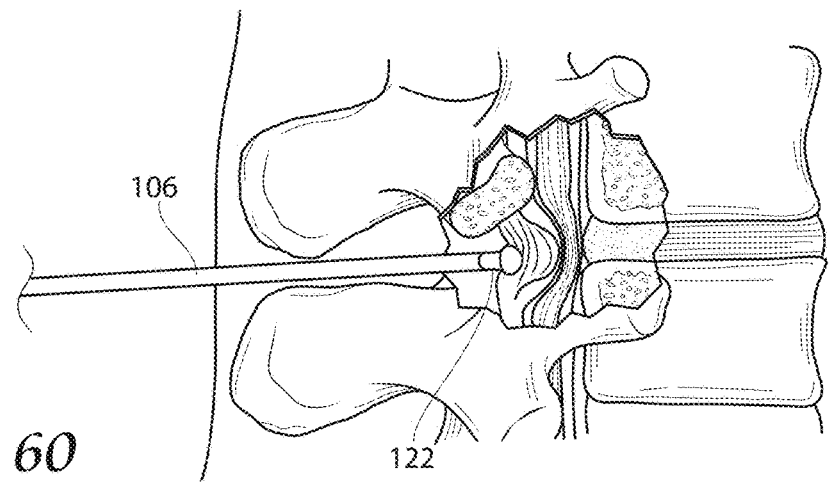

It is also contemplated that the styles 106 used in the process could have an end 126 that could either be sharp or angled (FIG. 59) or blunt (FIG. 60). For example, the use of the sharp end 128 stylet 106 may allow for the stylet 106 to be inserted through the skin and deep tissue without the use of a catheter 102 or secondary style 104. Once the guide wire 110 is properly positioned, the stylet could be removed, and be replaced with the blunt tip stylet, shown in FIG. 60, which would be useful in or around the foramen as it would not puncture dura or nerves. The cannulated sliding balloon 126 could then be placed and positioned as with previous inflatable members.

As such, the present invention provides several components that can work together to minimize injury and trauma during a stenosis procedure. It is understood that the various procedures could be incorporated with one another to carry out the medical procedures discussed herein. For example, the cannulated sliding balloon 126 or bendable arrangement shown in FIGS. 47-56 could be incorporated into the previous methods and still fall within the scope of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A method for treating impingement of a nerve of a spinal canal within a human body, said spinal canal including a vertebral foramen, the method comprising:
   providing a catheter;
   providing a bendable guide wire having an expandable member located within the catheter;
   introducing the guide wire into the general proximity of the impinged nerve;
   advancing the expandable member from the catheter into the spinal canal in a posterior to anterior position;
   expanding the expandable member;
   alleviating the pressure of the nerve impingement with the expanded expandable member; and
   removing the guide wire from the human body.

2. The method according to claim 1, wherein the guide wire is introduced with a cannula.

3. The method of claim 2, wherein an insert is inserted into the catheter through the cannula.

4. The method of claim 1, wherein the expandable member is removed after alleviating the pressure of the impinged nerve.

5. The method of claim 1, wherein the step of expanding the expandable member comprises increasing and decreasing the volume of the expandable member.

6. The method of claim 1, wherein the impingement is spinal stenosis.

7. The method of claim 6, wherein the catheter is introduced during a laminotomy.

8. The method of claim 6, wherein the catheter is introduced percutaneously.

9. The method of claim 1, further including the step of delivering an insert into the catheter near the inflatable member.

10. The method of claim 9, wherein the insert is inserted after the expandable member.

11. The method of claim 9, wherein the expandable member is delivered over the guide wire.

12. The method of claim 9, wherein the expandable member is delivered separately from the guide wire.

* * * * *